2013

(12) United States Patent
Sessler et al.

(10) Patent No.: US 8,580,845 B2
(45) Date of Patent: Nov. 12, 2013

(54) FUNCTIONALIZED EXPANDED PORPHYRINS

(75) Inventors: Jonathan L. Sessler, Austin, TX (US); Patricia J. Pantos, Providence, RI (US)

(73) Assignee: Board of Regents, The University of Texas System, Austin, TX (US)

( * ) Notice: Subject to any disclaimer, the term of this patent is extended or adjusted under 35 U.S.C. 154(b) by 258 days.

(21) Appl. No.: 12/664,524

(22) PCT Filed: Jun. 23, 2008

(86) PCT No.: PCT/US2008/067904
§ 371 (c)(1),
(2), (4) Date: Apr. 1, 2010

(87) PCT Pub. No.: WO2009/006075
PCT Pub. Date: Jan. 8, 2009

(65) Prior Publication Data
US 2010/0197031 A1 Aug. 5, 2010

Related U.S. Application Data

(60) Provisional application No. 60/937,676, filed on Jun. 29, 2007.

(51) Int. Cl.
*A61K 31/4025* (2006.01)
(52) U.S. Cl.
USPC .......................................... 514/422; 548/518
(58) Field of Classification Search
USPC ........................................................ 548/518
See application file for complete search history.

(56) References Cited

U.S. PATENT DOCUMENTS

| | | |
|---|---|---|
| 5,159,065 A | 10/1992 | Sessler et al. |
| 5,162,509 A | 11/1992 | Sessler et al. |
| 5,252,720 A | 10/1993 | Sessler et al. |
| 5,292,414 A | 3/1994 | Sessler et al. |
| 5,369,101 A | 11/1994 | Sessler et al. |
| 5,457,195 A | 10/1995 | Sessler et al. |
| 5,543,514 A | 8/1996 | Sessler et al. |
| 5,559,207 A | 9/1996 | Sessler et al. |
| 5,565,552 A | 10/1996 | Magda et al. |
| 5,569,759 A | 10/1996 | Sessler et al. |
| 5,587,371 A | 12/1996 | Sessler et al. |
| 5,599,928 A | 2/1997 | Hemmi et al. |
| 5,672,490 A | 9/1997 | Sessler et al. |
| 5,756,724 A | 5/1998 | Vogel et al. |
| 6,262,257 B1 | 7/2001 | Gale et al. |
| 6,602,702 B1 | 8/2003 | McDevitt et al. |
| 6,680,206 B1 | 1/2004 | McDevitt et al. |
| 6,984,734 B2 | 1/2006 | Sessler et al. |
| 7,041,819 B2 | 5/2006 | Sessler et al. |
| 7,122,572 B2 | 10/2006 | Gale et al. |
| 7,335,795 B2 | 2/2008 | Chang et al. |

OTHER PUBLICATIONS

Chemical and Engineering News, "Polymer Pulls Ion Pairs from Water", Rachel Petkewich, Oct. 27, 2008, vol. 86, No. 43, p. 9.
Poly(methyl methacrylate)s with pendant calizpyrroles: polymeric extractants for halide anion salts; Abdullah Aydogan et al., Chemcomm, 2008, pp. 1455-1457.
Poly(methyl methacrylate)s with Pendant Calixpyrroles and Crown Ethers: Polymeric Extractants for Potassium Halides, Angew. Chem. Int. Ed. 2008, pp. 9648-9652.
Akhlaghinia, B., "A new and convenient method of generating alkyl isocyanates from alcohols, thiols and trimethylsilyl ethers using triphenylphosphine/2,3-dichloro-5,6-dicyanobenzoquinone/Bu4NOCN," *Synthesis* 1955-1958, 2005.
Bröring, M., "A Facile and Efficient Method for the Preparation of New Meso-Arylbisdipyrrins," *Synthesis* 9:1291-1294, 2000.
Callaway, W.; Veauthier, J.M.; Sessler, J.L., "Schiff-Base Porphyrin and Expanded Porphyrin Analogues," *J Porphy Pthalocyan* 8:1-25, 2004.
D.L.; Hobart, D.E.; Neu, M.P., "Actinide Carbonate Complexes and Their Importance in Actinide Environmental Chemistry," *Chem Rev* 95:25-48, 1995.
Collins, G.E.; Lu, Q., "Microfabricated Capillary Electrophoresis Sensor for Uranium (VI)," *Anal Chim Acta* 436:181-189, 2001.
Davis, J. "Sapphyrins: Aggregation and Anion Binding Behavior in Polar, Protic Media," Ph.D. Dissertation, The University of Texas at Austin, Austin, 2001.
Goodey, A.; Lavigne, J.J.; Savoy, S.M.; Rodriguez, M.D.; Curey, T.; Tsao, A.; Simmons, G.; Wright, J.; Yoo, S.-J.; Sohn, Y.; Anslyn, E.V.; Shear, J.B.; Neikirk, D.P.; McDevitt, J.T., "Development of Multianalyte Sensor Arrays Composed of Chemically Derivatized Polymeric Microspheres Localized in Micromachined Cavities," *J Am Chem Soc* 123:2559-2570, 2001.
Goodey, A.; McDevitt, J.T., "Multishell Microspheres with Integrated Chromographic and Detection Layers for Use in Array Sensors," *J Am Chem Soc* 125:2870-2871, 2003.
Král, V.; Brucker, E.A.; Hemmi, G.; Sessler, J.L.; Kralova, J.; Bose, H., "A Non-Ionic Water-Soluble Pentaphyrin Derivative. Synthesis and Cytoxicity," *Bioorg Med Chem* 3:573-578, 1995.
Král, V.; Davis, J.; Andreivsky, A.; Kralová, J.; Aynytsyá, A.; Poucková, P.; Sessler, J.L., "Synthesis and Biolocalization of Water Soluble Sapphyrins," *J Med Chem* 45:1073-1078, 2002.
Kubo, Y.; Maeda, S.; Nakamura, M.; Tokita, S., "A Uranyl Ionsensitive Chromoionophore Based on Calix[6]arene,"*J Chem Soc Chem Commun* 1725-1726, 1994.
Lee, J.T. "Cyclo[n]pyrroles and Their Applications," Ph.D. Dissertation, The University of Texas at Austin, Austin, 2006.
Melfi, P.J.; Kim, S.K.; Lee, J.T.; Bolze, F.; Seidel, D.; Lynch, V.M.; Veauthier, J.M.; Gaunt, A.J.; Neu, M.P.; Ou, Z.; Kadish, K.M.; Fukuzumi, S.; Ohkubo, K.; Sessler, J.L., "Redox Behavior of Cyclo[6]pyrrole in the Formation of a Uranyl Complex," *Inorg Chem*, 46:5143-5145, 2007.

(Continued)

*Primary Examiner* — Brian McDowell
(74) *Attorney, Agent, or Firm* — Meunier Carlin & Curfman, LLC

(57) ABSTRACT

Disclosed are functionalized expanded porphyrins that can be used as spectrometric sensors for high-valent actinide cations. The disclosed functionalized expanded porphyrins have the advantage over unfunctionalized systems in that they can be immobilized via covalent attachment to a solid support comprising an inorganic or organic polymer or other common substrates. Substrates comprising the disclosed functionalized expanded porphyrins are also disclosed. Further, disclosed are methods of making the disclosed compounds (immobilized and free), methods of using them as sensors to detect high valent actinides, devices that comprise the disclosed compounds, and kits.

13 Claims, 15 Drawing Sheets

(56) References Cited

OTHER PUBLICATIONS

Rexhausen, H.; Gossauer, A., "The Synthesis of a New 22pi Electron Macrocycle: Pentaphyrin," *J Chem Soc Chem Commun* 275, 1983.

Roberto, J.; Diaz de la Rubia, T. *Report of the Basic Energy Sciences Workshop on Basic Research Needs for Advanced Nuclear Energy Systems*; Office of Basic Energy Sciences, DOE: Oct. 2006, pp. 123-128, full 421 page document available at http://www.er.doe.gov/bes/reports/abstracts.html#ANES.

Rohwer, H.; Rheeder, N.; Hosten, E., "Interactions of Uranium and Thorium with Arsenazo III in an Aqueous Medium," *Anal Chim Acta* 341:263-268, 1997.

Sawicki, M.; Siaugue, J.M.; Jacopin, C.; Moulin, C.; Burgada, R.; Meunier, S.; Baret, P.; Pierre, J.L.; Taran, F., "Discovery of Powerful Uranyl Ligands From Efficient Synthesis and Screening," *Chem Euro J* 11:3689-3697, 2005.

Schmuck, C.; Rupprecht, D.; Urban, C.; Walden, N., "Synthesis of Orthogonally Protected Pyrrole Tricarboxyilic Acid Derivatives: Versatile Building Blocks for Pyrrole-Containing Compounds," *Synthesis* 89-96, 2006.

Sessler, J.L.; Brucker, E.A., "The First 'crowned' Expanded Porphyrins," *Tet. Lett* 36:1175-1176, 1995.

Sessler, J.L.; Gorden, A.E.V.; Siedel, D.; Hannah, S.; Lynch, V.; Gordon, P.L.; Donohoe, R.J.; Tait, C.D.; Keogh, D.W., "New Actinide Expanded Porphyrin Complexes," *Inorg Chim Acta* 341:54-70, 2002.

Sessler, J.L.; Hemmi, G.; Mody, T.D.; Murai, T.; Burrell, A.K.; Young, S.W., "Texaphyrins: Synthesis and Applications," *Acc Chem Res* 27:43-50, 1994.

Sessler, J.L.; Hoehner, M., "An Efficient, High-Yield Preparation of Substituted 2,2'—Bipyrroles," *Synlett* 211-212, 1994.

Sessler, J.L.; Melfi, P.J.; Lynch, V.M., "Synthesis and Characterization of a Hexaphyrin(1.0.1.0.0.0) Bearing Both Meso and B-substituents," *J Porphy Pthalocyan* 11:287-293, 2007.

Sessler, J.L.; Melfi, P.J.; Pantos, G.D., "Uranium Complexes of Multidentate N-Donor Ligands," *Coord Chem Rev* 250:816-843, 2006.

Sessler, J.L.; Melfi, P.J.; Seidel, D.; Gorden, A.E.V.; Ford, D.K.; Palmer, P.D.; Tait, C.D., "Hexaphyrin(1.0.1.0.0.0): A New Colorimetric Actinide Sensor," *Tetrahedron* 60:11089-11097, 2004.

Sessler, J.L.; Melfi, P.J.; Tomat, E.; Callaway, W.; Huggins, M.T.; Gordon, P.L.; Keogh, D.W.; Date, R.W.; Bruce, D.W.; Donnio, B., "Schiff Base Oligopyrrolic Macrocycles as Ligands for Lanthanides and Actinides," *J Alloys and Compounds* 418:171-177, 2006.

Sessler, J.L.; Miller, R.A., "New Drugs with Diverse Clinical Applications in Radiation and Photdynamic Therapy," *Biochemical Pharmacology* 59:733-739, 2000.

Sessler, J.L.; Seidel, D., "Synthetic Expanded Porphyrin Chemistry," *Angew Chem Int Ed Engl* 42:5134-5175, 2003.

Sessler, J.L.; Seidel, D.; Vivian, A.E.; Lynch, V.; Scott, B.L.; Keogh, D.W., "Hexaphyrin(1.0.1.0.0.0): An Expanded Porphyrin Ligand for the Actinide Cations Uranyl ($UO_2^{2+}$) and Neptunyl ($NpO_2^+$)," *Angew Chim Int Ed Engl* 40:591-594, 2001.

Sessler, J.L.; Weghorn, S.J.; Lynch, V.; Fransson, K., "5,15,25-trisnor-Hexaphyrin: the First Structurally Characterized Linear Hexapyrrin," *J Chem Soc Chem Commun* 1289-1290, 1994.

Suresh, A.; Patre, D.K.; Srinivasan, T.G.; Rao, P.R.V., "A New Procedure for the Spectrophotometric Determination of Uranium(VI) in the Presence of a Large Excess of Thorium(IV)," *Spectrochim Acta* 58:341-347, 2002.

Wallace, D.M.; Leung, S.H.; Senge, M.O.; Smith, K.M., "Rational Tetraarylporphyrin Synthesis: Tetraarylporphyrins from the MacDonald Route," *J Org Chem* 58:7245-7257, 1993.

Wei, W.-H.; Wang, Z.; Mizuono, T.; Cortez, C.; Fu, L.; Sirisawad, M.; Naumovski, L.; Magda, D.; Sessler, J.L., "New Polyethyleneglycol-functionalized Texaphyrins: Synthesis and in vitro Biological Studies," *Dalton Trans* 1934-1942, 2006.

FUNCTIONALIZED EXPANDED PORPHYRINS

This application is related to and claims priority from U.S. provisional patent application No. 60/937,676, filed Jun. 29, 2007 and entitled "Functionalized Expanded Porphyrins," the disclosure of which is fully incorporated by reference herein for all purposes.

ACKNOWLEDGE OF GOVERNMENT SUPPORT

This invention was made with government support under DE-FG03-01ER15186 awarded by the Department of Energy. The government has certain rights in the invention.

BACKGROUND

Since the end of World War II, uranium and plutonium have become infamous household words synonymous with the potential for mass destruction. Nine countries now openly possess nuclear weapons and others are thought to have covert programs in various stages of development. Radiological weapons (i.e., "dirty bombs"), while less destructive than a nuclear weapon, could also cause substantial economic damage, endanger the public health, and lead to significant environmental contamination. There is thus an urgent demand for faster, more portable detection methods, including those that can be used to sense species, such as the high valent actinide cations, uranyl, neptunyl, and plutonyl, which are likely to be present on a relatively large scale under a variety of less-well-controlled conditions (i.e., following a spill or an untoward release).

The actinides (An) are easily hydrolyzed acidic metal ions that form strong complexes with common chelating agents (Clark et al., *Chem Rev* 95:25-48, 1995). The early actinides, between U and Am, are known for their diverse redox chemistry. The penta- and hexavalent oxidation states are generally the most common, especially for Np and Pu, wherein these actinides, like U(VI), exist as linear dioxocations. It is thus these species that are the most important in terms of sensor development for radioactive actinide cations.

To date, the problem of generating colorimetric actinide sensors, small molecules or receptors or constructs derived from them that change color when exposed to these species, has received relatively little attention. Two indicators that have been extensively studied are 2,2'-(1,8-dihydroxy-3,6-disulfonaphtylene-2,7-bisazo)-bisbenzenarsonic acid (AzIII) (Rohwer et al., *Anal Chim Acta* 341:263-268, 1997) and BrPADAP (Suresh et al., *Spectrochim Acta A* 58:341-347, 2002). These dyes have low limits of detection: 46 ppb for AzIII in aqueous media and 200 ppb for BrPADAP in ethanol. However, both suffer from drawbacks that make them less-than-ideal candidates for actinide detection. For instance, AzIII has a low selectivity for the actinides and, in fact, has a lower detection limit for the lanthanides (Ln) than for $UO_2^{2+}$ (e.g., 20 ppb with Gd(III)). This is problematic since the lighter lanthanides are produced in fission events and could act as interferants (Roberto et al., *Report of the Basic Energy Sciences Workshop on Basic Research Needs for Advanced Nuclear Energy Systems*; Office of Basic Energy Sciences, DOE: October, 2006, p 440). To avoid detection of the Ln rather than An cations, a pre-purification step to remove the lanthanides is generally necessary (Collins et al., *Anal Chim Acta* 436:181-189, 2001). BrPADAP suffers from the fact that it complexes Th(IV) strongly and displays reduced accuracy for uranium and plutonium in the presence of this cation Suresh et al., *Spectrochim Acta A* 58:341-347, 2002). Furthermore, this dye is not water-soluble and gives rise to only a slight color change upon metal complexation. Both AzIII and BrPADAP are difficult to functionalize, which further limits the scope of their utility.

Another potential colorimetric actinide sensor was reported by Kubo et al., who described the synthesis of a calix[6]arene functionalized with a single indoaniline chromophore (Kubo et al., *J Chem Soc, Chem Commun* 1725-1726, 1994). In the presence of $UO_2(OAc)_2$, a bathochromic shift was observed (from 628 to 687 nm) that was not seen in the presence of $Cs^+$, $Li^+$, $Sr^{2+}$, $Na^+$, $Ba^{2+}$, or $K^+$. To date, this system has not been functionalized for attachment to a solid support.

In work focused more on complexation than sensing, Taran and coworkers developed a combinatorial approach to the synthesis of uranyl receptors (Sawicki et al., *Chem Euro J* 11:3689-3697, 2005). These researchers screened 96 potential uranyl complexing agents using a competitive displacement strategy. Analysis via fluorescence titrations confirmed that the best system obtained in this way could be used to detect uranyl concentrations of less than $10^{-11}$ M; selectivity over alkali and alkali earth cations, but not $Fe^{3+}$, was also observed. This system, however, did not permit direct detection via an easy-to-see color change.

In light of the above, there is a need for improved spectrometric actinide sensors. Particularly advantageous would be systems that could be attached to solid supports because this permits the conversion of molecular entities that display a spectrometric response in the presence of actinides into actual sensing devices. These and other needs are addressed herein through the production of certain functionalized expanded porphyrins, e.g., β-pyrrolic-, meso-, and β-pyrrolic and meso-substituted isoamethyrins.

SUMMARY

In accordance with the purposes of the disclosed materials, compounds, compositions, articles, and methods, as embodied and broadly described herein, the disclosed subject matter, in one aspect, relates to compounds and compositions and methods for preparing and using such compounds and compositions. In a further aspect, disclosed herein are functionalized expanded porphyrins. In various examples, the compounds disclosed herein can be used as synthetic receptors that act as spectrometric sensors for the uranyl, neptunyl, and/or plutonyl cations (so-called high-valent actinide cations). The disclosed functionalized expanded porphyrins have the advantage over unfunctionalized systems in that they can be immobilized via covalent attachment to a solid support comprising an inorganic or organic polymer or other common substrates. Substrates comprising the disclosed functionalized expanded porphyrins are also contemplated herein. Further disclosed herein are methods of making the disclosed compounds (immobilized and free), methods of using them as sensors to detect high valent actinides, devices that comprise the disclosed compounds, and kits.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
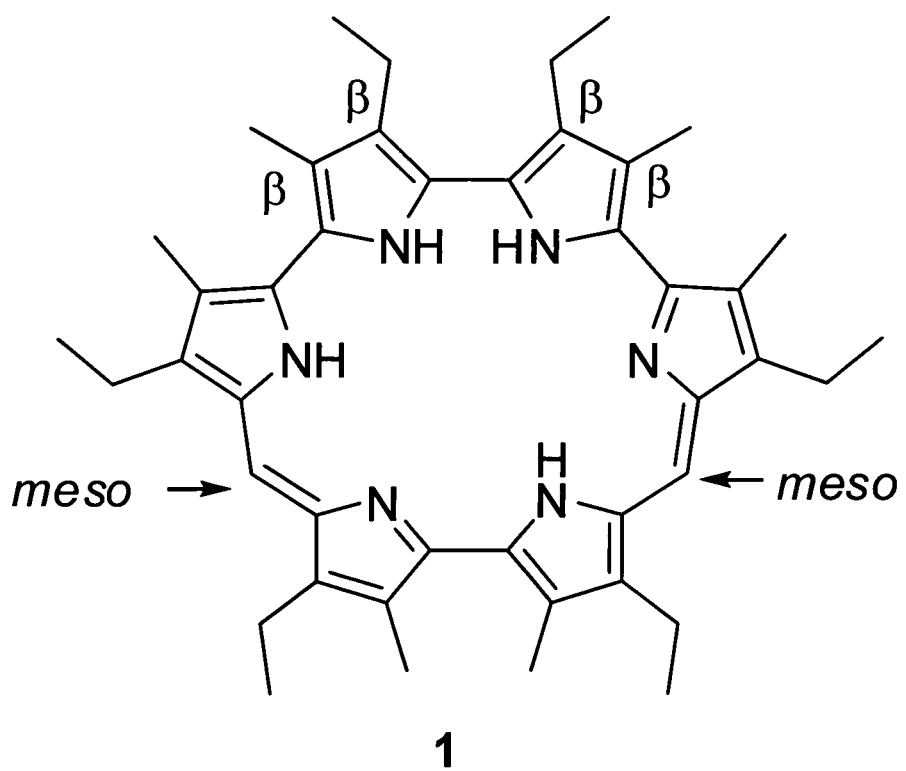
FIG. 1 is a chemical structure of an unfunctionalized isoamethyrin 1.

The materials, compounds, compositions, articles, devices, and methods described herein may be understood more readily by reference to the following detailed description of specific aspects of the disclosed subject matter and the Examples included therein and to the Figures.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and, unless a particular term is specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an isoamethyrin" includes mixtures of two or more such isoamethyrins, reference to "the substrate" includes mixtures of two or more such substrates, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and claims to parts by weight of a particular element or component in a composition or article denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "spectrometric" is used herein to mean anything that results in a discernible change in color and/or anything that gives a measurable change in spectroscopic properties, either absorption intensity or position, emission (singlet-fluorescence or triplet-phosphorescence) intensity or position, or excited state lifetime. It is not meant to be limited by the specific method of detection.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

A "residue" of a chemical species, as used in the specification and concluding claims, refers to the moiety that is the resulting product of the chemical species in a particular reaction scheme or subsequent formulation or chemical product, regardless of whether the moiety is actually obtained from the chemical species.

"$A^1$," "$A^2$," "$A^3$," and "$A^4$" are used herein as generic symbols to represent various specific substituents. These symbols can be any substituent, not limited to those disclosed herein, and when they are defined to be certain substituents in one sentence it does not mean that, in another sentence, they cannot be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. A "lower alkyl" group is an alkyl group containing from one to six carbon atoms (i.e., $C_1$-$C_6$).

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The term "alkoxy" as used herein is an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A'A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)A' or —C(O)OA$^1$, where A$^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, a substituted or unsubstituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$^a$—, where A$^1$ and A$^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "hydroxyl" as used herein is represented by the formula —OH.

The term "ketone" as used herein is represented by the formula A$^1$C(O)A$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "isocyanate" as used herein is represented by the formula —N=C=O.

The term "silyl" as used herein is represented by the formula —SiA$^1$A$^2$A$^3$, where A$^1$, A$^2$, and A$^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, S(O)$_2$A$^1$, —OS(O)$_2$A$^1$, or —OS(O)$_2$OA$^1$, where A$^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R''$," and "L," as used herein can, independently, possess one or more of the groups listed above. For example, if L is a polyether group, one of the hydrogen atoms of the polyether group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "a polyether group comprising an alkene group," the alkene group can be incorporated within the backbone of the polyether group. Alternatively, the alkene group can be attached to the backbone of the polyether group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of substituents on the composition are discussed, each and every combination and permutation that are possible are specifically contemplated unless specifically indicated to the contrary. Thus, if a class of components or moieties A, B, and C are disclosed as well as a class of components or moieties D, E, and F and an example of a composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Disclosed herein are compositions that comprise a functionalized expanded porphyrin that is capable of producing a spectrometric response, for example, a change in visible color or spectroscopic signature, when exposed to cations of the actinide series. In one aspect, disclosed herein are compositions that comprise a functionalized expanded porphyrin that comprises a linker moiety attached to one or more of the β-pyrrolic positions. In a further aspect, disclosed herein are compositions that comprise a functionalized expanded porphyrin that comprises a linker moiety attached to one or more of the meso-positions, if present. In a still further aspect, disclosed herein are compositions that comprise a functionalized expanded porphyrin that comprises a linker moiety attached to one or more of the β-pyrrolic positions and one or more of the meso-positions.

Expanded porphyrins are oligopyrrolic macrocycles that can be considered as larger versions of the naturally occurring tetrapyrrolic pigments, porphyrin, chlorophyll, and coenzyme B12 (Sessler et al., *Angew Chem Int Ed Engl* 42:5134-5175, 2003). Certain expanded porphyrins have emerged as very promising complexants for common radioactive ions in that often substrate binding is correlated with a dramatic color change (Sessler et al., *Angew Chem Int Ed Engl* 40:591-594, 2001; Sessler et al., *Inorg Chim Acta* 341:54-70, 2002; Sessler et al., *Tetrahedron*, 60:11089-11097, 2004; Sessler et al., *Coord Chem Rev* 250:816-843, 2006; Sessler et al., *J Alloys Compds* 408:171-177, 2006; Melfi et al., *Inorg Chem* 46:5143-5145, 2007).

To make these systems suitable for use in the field, they can be functionalized such that they can be immobilized onto solid supports. Such attachment is useful in that it would prevent the expanded porphyrin from washing off a substrate; it would also allow for the generation of sensor devices, including those based on beads or optical probes.

The functionalized expanded porphyrins disclosed herein can be empirically represented by the following formula:

EP-L where EP is an expanded porphyrin and L is a functional group that can be used to link the expanded porphyrin to a solid support (i.e., a "linker moiety" herein). It is understood, that the expanded prophyrin can (and often does) contain more than one linker moiety L. The linker moiety can react with and form a bond to a solid support, thus linking the functionalized expanded prophyrin to the support. Suitable examples of linker moieties are disclosed herein, examples of which include, but are not limited to, an alkyl ester, activated carboxylic acid ester, carboxylic acid or salt thereof, acyl halide, thioester, alcohol, amine, substituted amine, amide, substituted amide, azide, isocyanate, thioisocyanate, thiol, disulfide, halide, ether, substituted ether, carbamate, carbonate, alkene, alkyne, or anhydride. Accordingly, when the functionalized expanded porphyrins are immobilized onto a solid support, they can be empirically represented by the formula:

EP-L-Support

As noted, the disclosed compositions comprise functionalized expanded porphyrins. And like their unfunctionalized counterparts, the disclosed compositions can complex high valent actinides. Suitable examples of expanded porphyrins that can be functionalized as disclosed herein include, but are not limited to, isoamethryin, oxasapphyrin, dioxamethryin, pentaphyrin, amethyrin, alaskaphyrin, huggisphyrin, and cyclo[6]pyrrole.

Isoamethyrins

Figure 2:
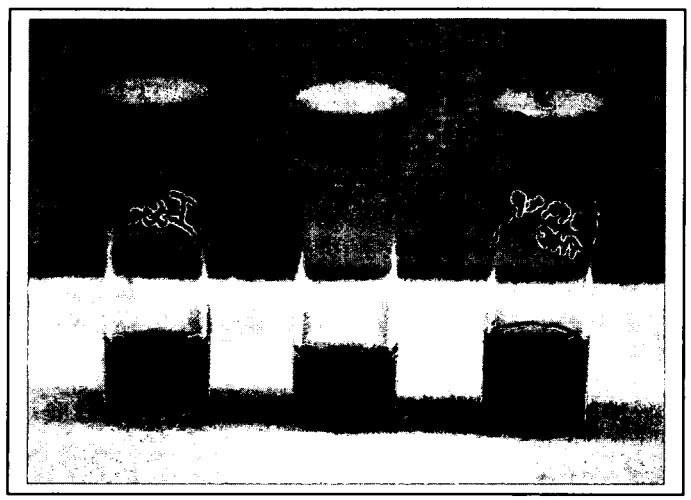
FIG. 2 is a photograph of solutions of unfunctionalized isoamethyrin 1 in a 1:1 (v./v.) mixture of MeOH:CH$_2$Cl$_2$:free base (center), color changes produced after addition of HCl (right) and two equivalents of aqueous plutonyl chloride (left).

In specific examples, the expanded porphyrin is isoamethyrin (hexaphyrin(1.0.1.0.0.0); FIG. 1, also referred to herein as isoamethyrin 1), which is a system that can produce a particularly dramatic color change when exposed to high valent actinide cations. To date, isoamethyrin has been the subject of extensive study as a free-standing actinide sensor. This particular system undergoes spontaneous oxidation to a more highly colored aromatic form upon coordination with the uranyl, neptunyl, or plutonyl cations. The net result is a dramatic color change (cf. FIG. 2) (Sessler et al., *Angew Chem Int Ed Engl* 40:591-594, 2001). Dilution experiments revealed that naked eye detection of the uranyl cation was possible down to the 20 ppm level (Sessler et al., *Tetrahedron* 60:11089-11097, 2004). Further, competition studies served to demonstrate that, with the exception of copper(II), the uranyl cation is complexed preferentially over other metal salts, such as Gd(III), Zn(II), Fe(III), and Th(IV) (Sessler et al., *Inorg Chim Acta* 341:54-70, 2002; and Sessler et al., *J Alloys Compds* 408:171-177, 2006). In fact, none of these latter cations give rise to a discernible color change (Sessler et al., *Tetrahedron* 60:11089-11097, 2004). These findings have made isoamethyrin attractive as a spectrometric sensor for the dioxo actinide cations, $UO_2^{2+}$, $NpO_2^+$, $NpO_2^{2+}$, $PuO_2^+$, and $PuO_2^{2+}$. Unfortunately, unfunctionalized isoamethyrin when simply contacted with a solid support (e.g., evaporation onto filter paper in this example), tends to smear when exposed to aqueous solutions of uranyl cation. This deficiency is overcome by the methods and compositions disclosed herein, which involve the preparation of functionalized isoamethyrins and their attachment onto a solid support through the formation of one or more covalent bonds.

Figure 3:
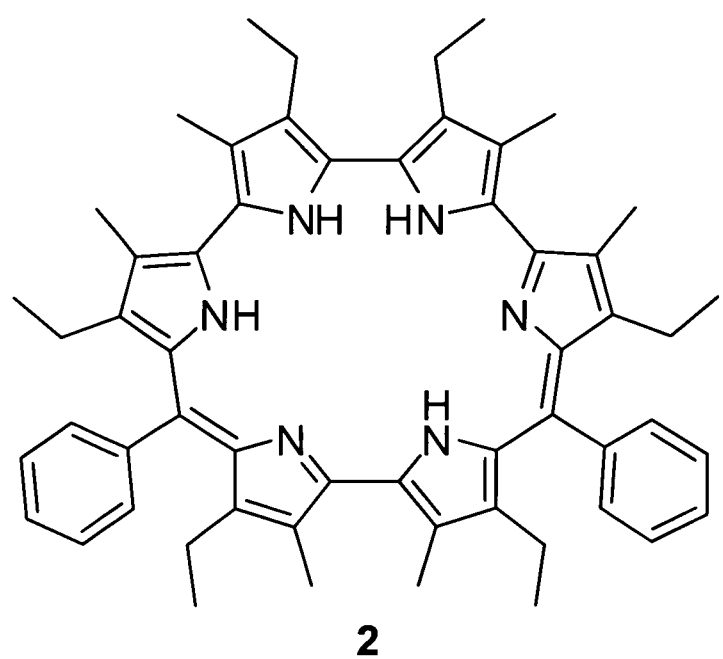
FIG. 3 is a chemical structure of a meso-substituted isoamethyrin 2.

Such attachment or so-called covalent tethering requires the synthesis of suitably functionalized isoamethyrin compounds. While certain functionalized expanded porphyrins are known (Rexhausen and Gossauer, *J Chem Soc Chem Commun* 275, 1983; Kral et al., *Bioorg Med Chem* 3:573-578, 1995; Sessler et al., *Tet Lett* 36:1175-1176, 1995; Callaway et al., *J Porph Phthalocyan* 8:1-25, 2004; Wei et al., *J Chem Soc Dalton Trans* 1934-1942, 2006; Sessler et al., *Angew Chem Int Ed Engl* 42:5134-5175, 2003; and are described in U.S. Pat. Nos. 5,457,195, 5,159,065, 5,252,720, 5,369,101, 5,543,514, 5,599,928, 5,569,759, and 5,587,37, which are all incorporated in their entireties herein by reference), the methods used to obtain such functionalized systems, involving use of either 1) a substituted tripyrrane or 2) the attachment of substituents to the meso positions, are generally unsuitable for producing functionalized isoamethyrins. The first of these approaches is unworkable because isoamethyrin lacks a tripyrrane moiety, while the second was specifically tested by the inventors and found to give rise to isoamethyrin products that failed to produce a well-characterized uranium complex when exposed to the uranyl cation (vide infra; see also: Sessler et al., *J Porph Phthalocy* 11:287-293, 2007). Specifically, as described in Example 1, the test meso-substituted isoamethyrin 2 (see FIG. 3) was prepared, which failed to produce a dramatic color change when exposed to the uranyl cation.

Thus, in one aspect, disclosed herein are isoamethyrins functionalized at one or more of the β-pyrrolic positions with a linker moiety that can be used to attach the isoamethyrin to a solid support. When functionalized at two of the β-pyrrolic positions, these compounds have the following general formula:

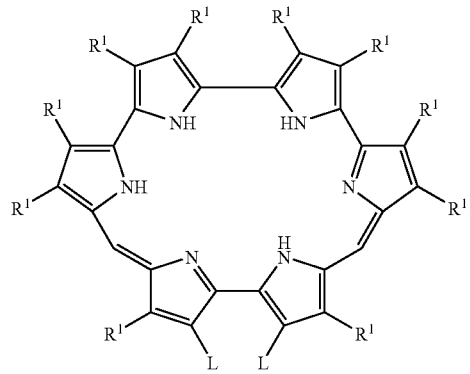

wherein each $R^1$ is, independent of the others, hydrogen, a substituted or unsubstituted alkyl, cycloalkyl, alkoxy, alkenyl, cycloalkenyl, alkynyl, cycloalkynyl, aryl, or heteroaryl; and each L is, independent of the other, a moiety comprising an alkyl ester, activated carboxylic acid ester, carboxylic acid or salt thereof, acyl halide, thioester, alcohol, amine, substituted amine, amide, substituted amide, azide, isocyanate, thioisocyanate, thiol, disulfide, halide, ether, substituted ether, carbamate, carbonate, alkene, alkyne, or anhydride group. Also contemplated are compounds where one or more of the $R^1$ substituents is replaced by another linker moiety L. In a specific, example, each $R^1$ can be, independent of the others, methyl or ethyl. In another example, each L can be a propionate ester (e.g., $-CH_2CH_2CO_2CH_3$), a propionic acid, or hydroxypropyl group.

In a further aspect, disclosed herein are isoamethyrins functionalized at one or more of the meso-positions with a linker moiety that can be used to attach the isoamethyrin to a solid support, with the proviso that the one or more meso substituents are not phenyl. When functionalized at two of the meso-positions, these compounds have the following general formula:

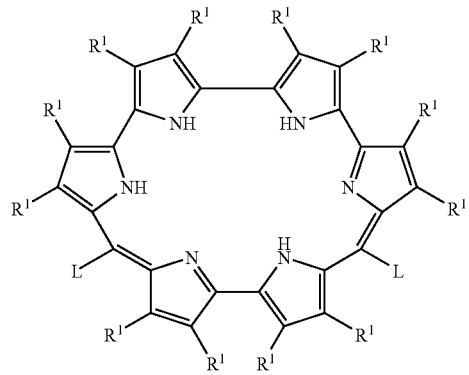

where each $R^1$ and L is as defined above.

In a still further aspect, disclosed herein are isoamethyrins functionalized at one or more of the β-pyrrolic positions and one or more of the meso-positions with a linker moiety that can be used to attach the isoamethyrin to a solid support, with the proviso that the one or more meso substituents are not phenyl. When functionalized at two of the β-pyrrolic positions and two of the meso-positions, these compounds have the following general formula:

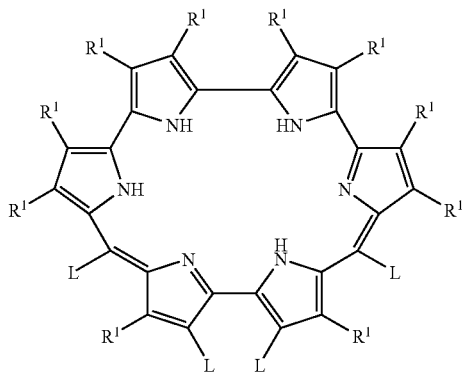

where each $R^1$ and L is as defined above.

The disclosed functionalized isoamethyrins can be prepared by a new approach, as detailed in Example 2, which involves the use of a functionalized bipyrrole fragment. Functionalized bipyrrole fragments of structure 7-9 are described in the Ph.D. Dissertation of Jeong Tae Lee, incorporated in its entirety herein by reference (Lee, "Cyclo[n]pyrroles and Their Applications," Ph.D. Dissertation, The University of Texas at Austin, May, 2006). An improvement in the yield of the substituted bipyrrole is also disclosed herein. It involves the finding that pyrrole 3 can be converted into the free acid 4 directly in one step using an oxidation procedure recently published by Schmuck, as shown in Scheme 1 (Schmuck et al., *Synthesis* 89-96, 2006). Standard chemistry, such as that disclosed in Sessler and Hoehner (*SYNLETT* 211-212, 1994) and U.S. Pat. No. 5,756,724, incorporated in their entireties herein by reference, can then be used to convert this pyrrole-2-carboxylic acid into the bipyrrole 7, which can be converted to the diformyl bipyrrole 10 after saponification, decarboxylation and Vilsmeier-Haack formylation.

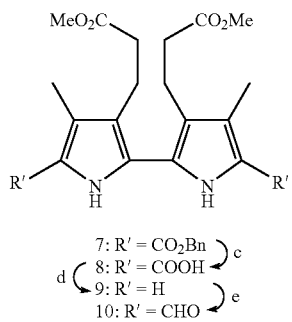

Conditions: a) $SO_2Cl_2$; b) $I_2$, KI, $H_2O$, methanol; c) $H_2$, Pd/C, THF; d) TFA; e) DMF, $POCl_3$.

From this latter precursor (i.e., diformyl pyrrole 10), a diester functionalized isoamethyrin expanded porphyrin 13, can be made in two steps, as shown in Scheme 2.

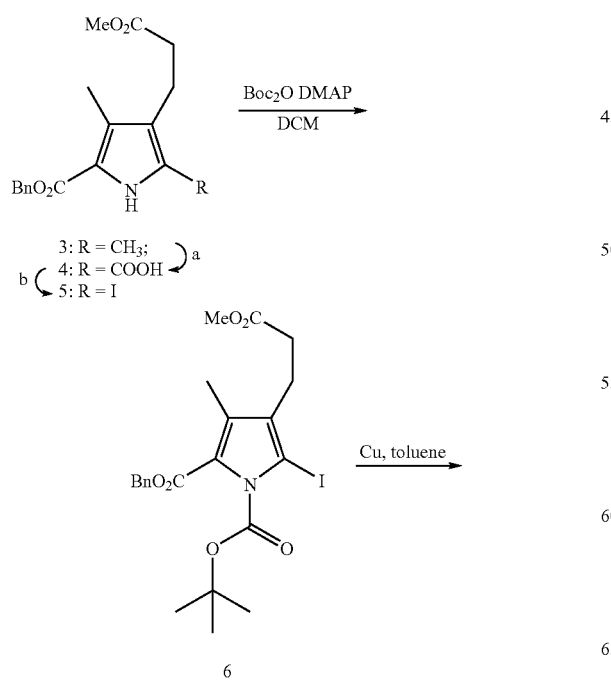

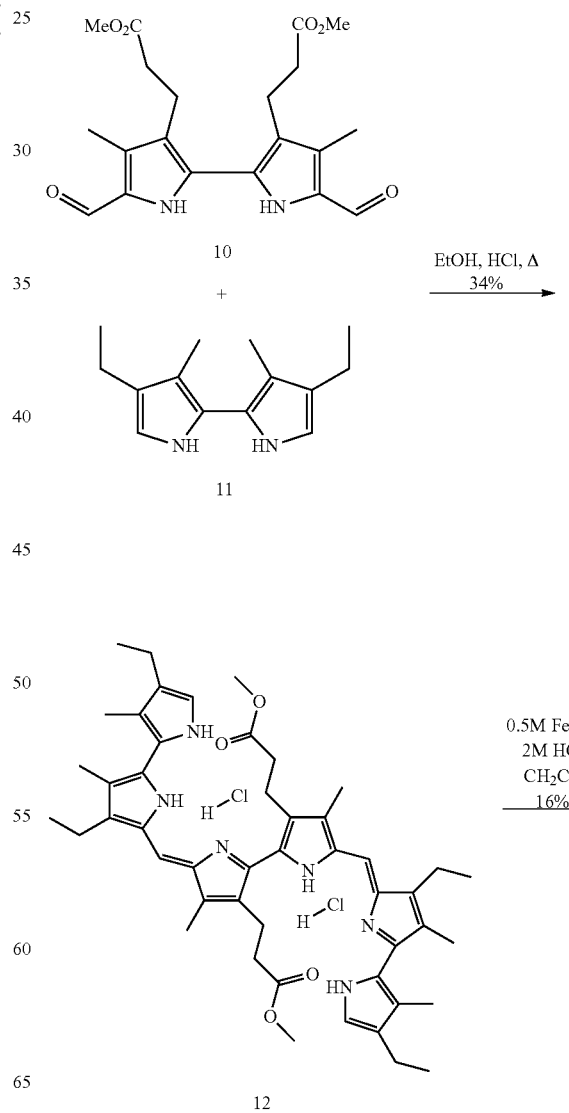

-continued

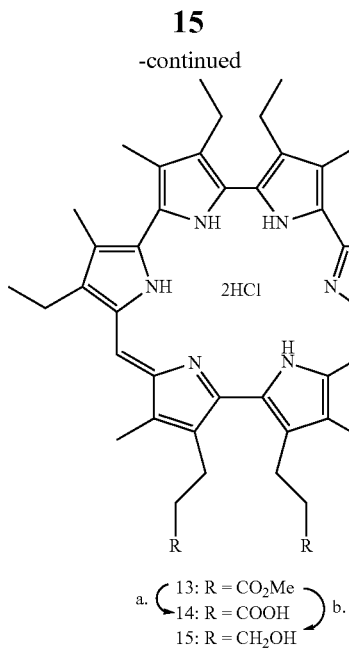

a. 13: R = CO₂Me
14: R = COOH    b.
15: R = CH₂OH

Conditions: a) TFA, HCl (conc.); b) DiBAlH, toluene.

In Schemes 1 and 2, the linker moiety of the functionalized isoamethyrin is a methyl-proponate moiety. This moiety can be used to attach the isoamethyrin to a solid support or transformed into other reactive moieties, which can then react with and form a bond to a solid support. Other suitable linker moieties can also be used, as are disclosed elsewhere herein.

Figure 4:
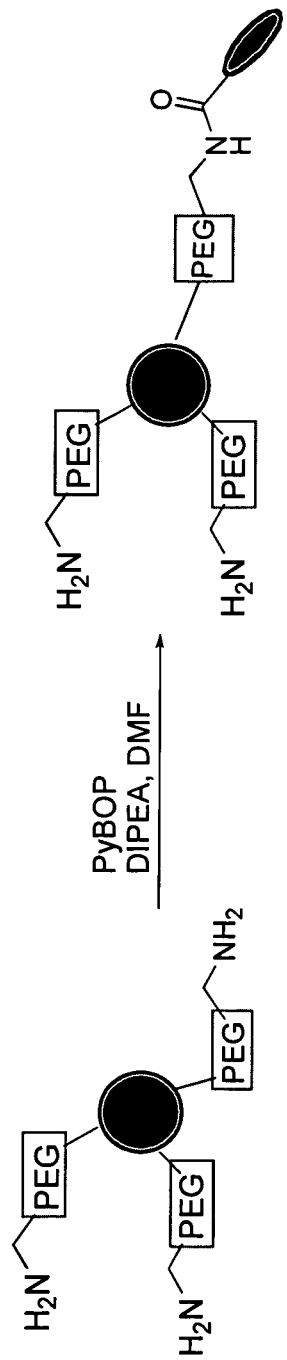
FIG. 4 is a schematic of the attachment of isoamethyrin 14 to a TENTAGEL™ bead (the shaded disk represents the macrocycle).

The functionalized isoamethyrin 13 can be hydrolyzed to the corresponding free acid 14 and immobilized onto a TG (TENTAGEL™) amino resin "bead" using the procedure of McDevitt and Anslyn, as described in McDevitt et al., *J Am Chem Soc* 123:2559-2570, 2001; Goodey et al., *J Am Chem Soc* 125:2870-2871, 2003, McDevitt et al., International PCT Publication No. WO 2004/072613, and U.S. Pat. Nos. 6,602,702 and 6,680,206, which are incorporated in their entireties herein by reference (FIG. 4). The Color changes were observed for this bead under different conditions. Specifically, a discernable color difference was seen upon exposure for more than one day of the functionalized bead to uranyl cations (0.02 M methanoic solution of uranyl nitrate), HCl (1 M), or 10% aqueous NaOH. Importantly, the color change produced in this way is distinct from that seen in the presence of protons, thereby establishing the utility of this functionalized isoamethyrin-derived system as being a viable uranyl sensing device.

The diester 13 can also be reduced to the corresponding diol 15. This produces an isoamethyrin functionalized with two nucleophile groups that can be attached to a solid support via, inter alia, formation of ester, carbonate, or carbamate linkages. The generation and use of diol 15 and other hydroxy-functionalized isoamethyrins is thus contemplated herein.

Cyclo[6]pyrroles

Figure 7:
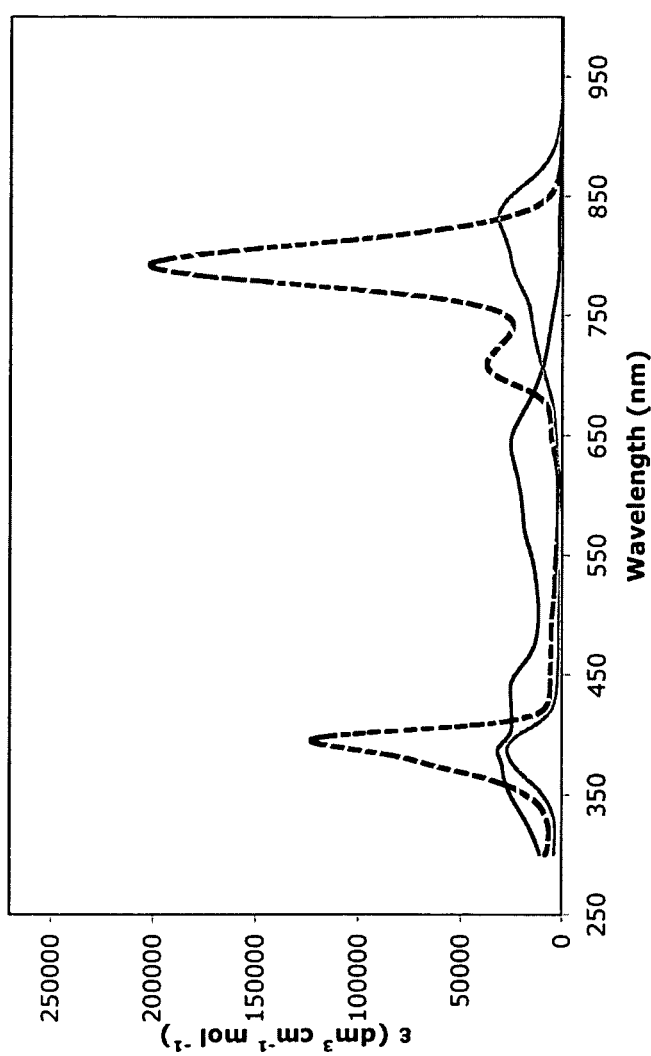
FIG. 7 is the UV-visible spectra of H$_2$23$^{2+}$.2Cl$^-$ (dashed line), the free base (neutral) form of compound 23 (grey line), and oxidized, nonaromatic uranyl complex (solid black line) recorded in CH$_2$Cl$_2$.

Cyclo[6]pyrrole 23 (Scheme 3) has been found to form a very stable uranyl complex (Melfi et al., *Inorg Chem* 46:5143-5145, 2007) while undergoing a significant loss in absorption intensity upon metal complexation (cf. FIG. 7).

Scheme 3: Synthesis of unfunctionalized cyclo[6]pyrrole 23 and method for preparing a functionalized derivative 24.

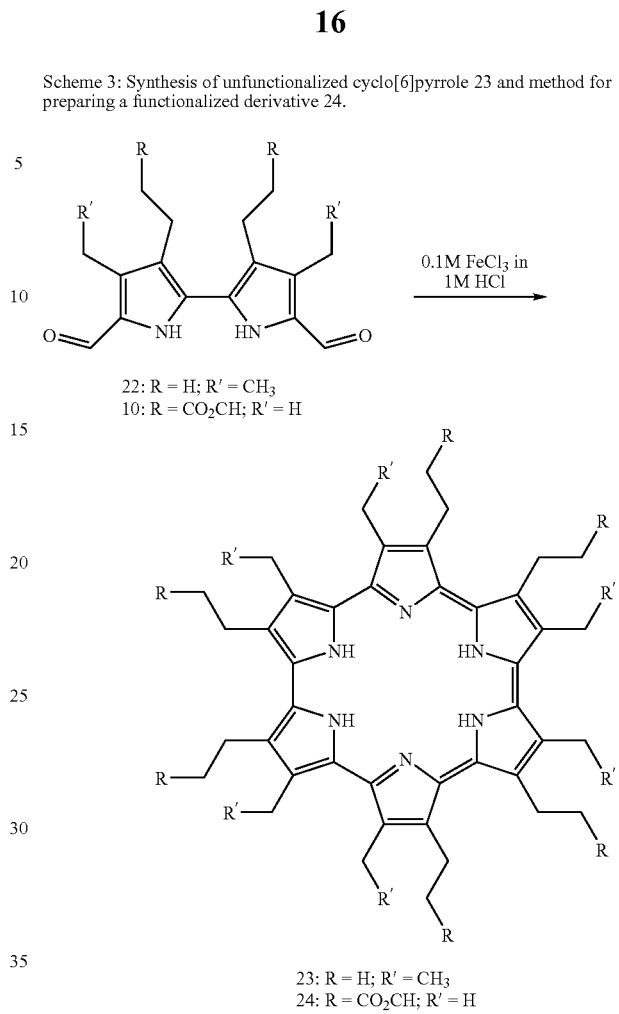

22: R = H; R′ = CH₃
10: R = CO₂CH; R′ = H

23: R = H; R′ = CH₃
24: R = CO₂CH; R′ = H

It thus stands in marked contrast to the β-pyrrole substituted isoamethyrin, which displays an increase in intensity upon exposure to $UO_2^{2+}$, $NpO_2^+$, and $PuO_2^+/PuO_2^{2+}$. Thus, functionalization of these systems can provide systems suitable for attachment to a solid support and the development of actinide sensing devices. So in one aspect, disclosed herein are functionalized cyclo[6]pyrroles having the following general formula:

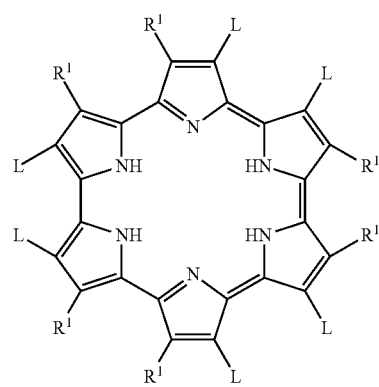

wherein each $R^1$ is, independent of the others, hydrogen, a substituted or unsubstituted alkyl, cycloalkyl, alkoxy, alkenyl, cycloalkenyl, alkynyl, cycloalkynyl, aryl, or heteroaryl;

and each L is, independent of the others, a moiety comprising an alkyl ester, activated carboxylic acid ester, carboxylic acid or salt thereof, acyl halide, thioester, alcohol, amine, substituted amine, amide, substituted amide, azide, isocyanate, thioisocyanate, thiol, disulfide, halide, ether, substituted ether, carbamate, carbonate, alkene, alkyne, or anhydride group. In a specific, example, each $R^1$ can be, independent of the other, methyl or ethyl and each L can be propionate ester (e.g., —$CH_2CH_2CO_2CH_3$), a propionic acid, or hydroxypropyl group.

In light of U.S. Pat. Nos. 6,602,702 and 6,680,206, the availability of more than one spectrometric chemosensor for the actinide cations can allow for the construction of more sensitive array-based detection systems. Such arrays could be produced, for instance, by generating solid supports to which are covalently attached both functionalized isoamethyrins and functionalized cyclo[6]pyrroles. The requisite functionalized cyclo[6]pyrroles can be obtained, for instance, by subjecting the same substituted bipyrrole precursor 10 used to obtain the β-pyrrole substituted isoamethyrin to the oxidative ring-forming coupling conditions used to obtain the unfunctionalized cyclo[6]pyrrole framework. This would produce the ester substituted cyclo[6]pyrrole 24, as shown in Scheme 3. Once in hand, the tetraester 24 can be further functionalized, including hydrolysis to the corresponding acid derivative or reduction to the corresponding tetraol.

Other Expanded Porphyrins

Figure 5:
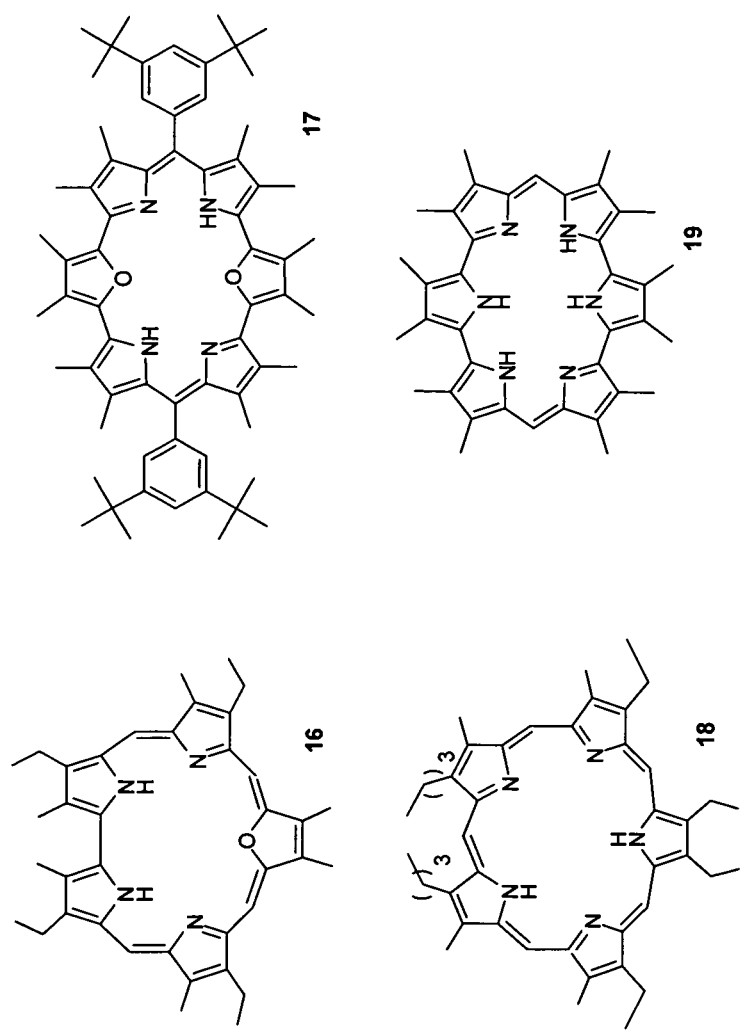
FIG. 5 is a group of chemical structures of expanded porphyrins that act as spectrometric actinide cation sensors, as disclosed herein.
Figure 6:
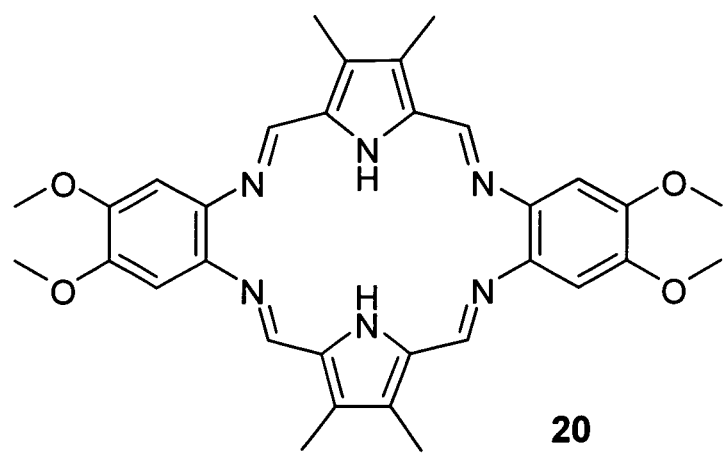
FIG. 6 is a pair of chemical structures of Schiff base-type expanded porphyrins that can act as spectrometric actinide cation sensors, as disclosed herein.
Figure 6:
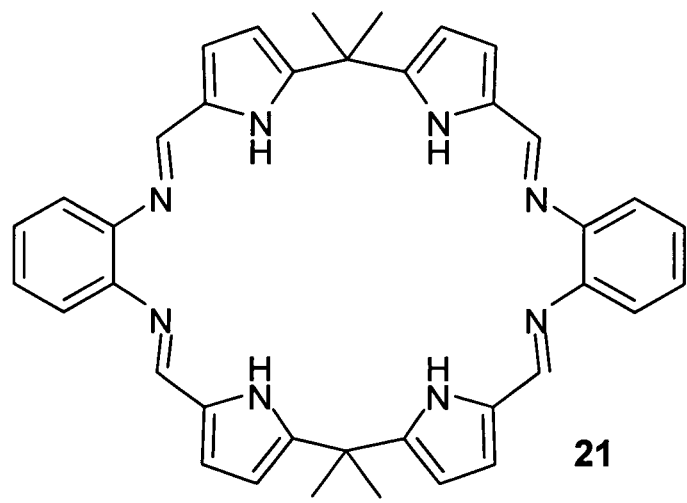

In addition to isoamethyrin and cyclo[6]pyrrole, a number of other expanded porphyrins, namely oxasapphyrin 16, dioxamethyrin 17, pentaphyrin 18, and amethyrin 19 (cf. FIG. 5 for structures), undergo a change in color when exposed to $UO_2^2$, both oxidation states of the neptunyl cation ($NpO_2^{2+}$ and $NpO_2$), and a $PuO_2^+/PuO_2^{2+}$ mixture (Sessler et al., Inorg Chim Acta 341:54-70, 2002). The Schiff base systems alaskaphyrin 20 and huggisphyrin 21 (cf. FIG. 6 for structures) also change color upon exposure to either $NpO_2^{2+}$ or $PuO_{2+}/PuO_2^{2+}$, as described in Sessler et al., incorporated in its entirety herein by reference (Sessler et al., J Alloys Compds 418:171-177, 2006).

As noted above, a number of expanded porphyrins besides isoamethyrin and cyclo[6]pyrrole produce a color change when exposed to the uranyl or neptunyl cations. These spectrometric systems can be functionalized to produce expanded porphyrin-bearing solid supports that act as actinide cation sensing systems. Many methods can be employed to obtain the requisite functionalized expanded porphyrins. By way of example, a synthesis of a functionalized pentaphyrin 25, bearing β-pyrrolic propoxy groups, is shown in Scheme 4; starting with compound 3 and proceeding through the tripyrrane 26, gives the target.

Scheme 4: Functionalized pentaphyrin 25.

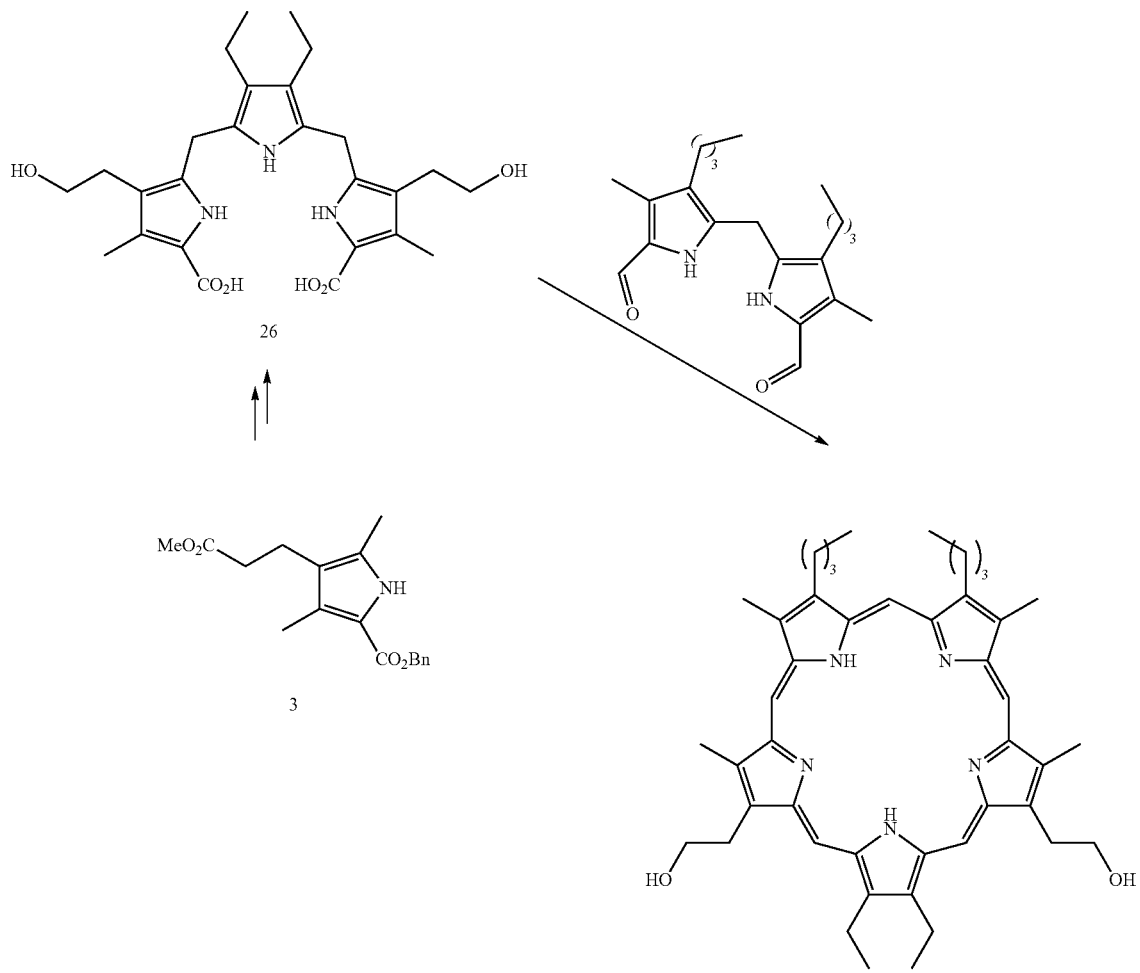

Similar modification strategies are applicable to amethyrins 17 and 19, as well as to oxasapphyrin 16. In all cases, the hydroxy substituents can be converted to other common functional groups through standard manipulations, e.g., oxidation to produce aldehyde or acid moieties, reaction with thionyl chloride or phosphorus tribromide to produce the corresponding halide derivatives, from whence a greater range of derivatives becomes possible.

Macrocyclic Schiff bases (alaskaphyrin 30 and huggisphyrin 29), in addition to permitting β-pyrrolic derivitization as per the above, can be modified through functionalization of the phenyl rings. For instance, the attachment of various ether derivatives to the 4- or 4 and 5 positions of 1,2-diaminobenzene precursors has been used to effect to produce modified texaphyrins, which are described in Sessler et al., *Acc Chem Res* 27:43-50, 1994; Sessler et al., *Biochemical Pharmacology* 59:733-739, 2000, and U.S. Pat. Nos. 5,162,509, 5,252,720, 5,292,414, 5,559,207, 5,565,552, 5,587,371, 5,672,490, and 5,599,928, which are all incorporated in their entireties herein by reference. As described in these references, there are several entries into the key precursors, one embodiment of which involves the use of dinitrophenols and catechols and functionalization via ether bond formation (as used in the case of the texaphyrins). However, one of skill in the synthetic organic chemical arts would appreciate that a number of alternative functionalization strategies can be pursued successfully, including via Sonogashira coupling to a bromo dinitrobenzene derivative, a strategy that would allow attachment of, e.g. functionalized alkynes. Reduction of the dinitro functionality would provide the diamine required for macrocyclization.

Linker Moieties

Although viewed as being particularly advantageous for attachment to solid supports, the substituted actinide sensing expanded porphyrins disclosed herein need not be limited to carboxylic acids, esters, alcohols, and amines. Standard functional group interconversions can be used to interconvert these core functional groups or transform them to others that may prove useful in the case of certain attachment protocols. For instance, esters can be converted to amides by treatment with ammonia or amines under equilibrium-favoring conditions (e.g., acid catalysis). Likewise, amine substituted expanded porphyrins can be produced from the corresponding acid functionalized systems with loss of a carbon via the Hoffmann, Curtius, or Schmidt rearrangements. Amine derivatives containing the same number of carbons as in the original products can be produced by converting an alcohol substituted system to the corresponding halide by treatment with, e.g., thionyl chloride or phosphorus tribromide, followed by displacement with azide and reduction via, e.g., hydrogenation or treatment with an active hydride reagent (e.g., lithium aluminum hydride). Chain extended amines can be produced by treating the intermediate alkyl halides with acrylonitrile followed by reduction. Thiols can be produced from these intermediate alkyl halides by treating with sodium sulfide. Esters and thioesters can be produced from alcohols and thiols by treating with carboxylic acids or activated forms thereof. Ethers and thioethers can be produced from these same starting materials via standard organic transformations that would be appreciated to one of skill in the art, e.g., Williamson ether synthesis. Mixed anhydrides and mixed carbonates can be obtained from appropriate application of other anhydrides or activated carbonates. Aldehydes could be produced by subjecting primary alcohols to oxidation in the absence of water using, e.g., pyridinium chlorochromate, while carboxylic acids can be produced by subjecting these same primary alcohols to oxidation in the presence of water.

Nitriles could be produced by subjecting the intermediate alkyl halide derivatives described above to displacement with a source of cyanide anion. Isocyanates can also be produced from the amine derivatives by reaction with phosgene or equivalents. Furthermore, recent reports have demonstrated the conversion of alcohols to alkyl isocyanates when reacted with triphenylphosphine, DDQ (2,3-dichloro-5,6-dicyanobenzoquinone), and $Bu_4NOCN$ (Akhlaghinia, *Synthesis* 1955-1958, 2005).

Linker moieties can be, in some examples, alkenes or alkynes, which can react with suitable solid supports via a 3+2 or 2+2 cycloaddition reaction.

In general, when the linker moiety comprises one or more nucleophilic functional groups, they can react with electrophilic functional groups on the solid support, forming a bond. Alternatively, when the linker moiety comprises one or more electrophilic functional group, they can react with nucleophilic functional groups on the solid support, forming a bond. Still further, when the linker comprises both nucleophilic and electrophilic functional groups, they can react with solid supports containing either electrophilic or nucleophilic functional groups, forming a bond.

Nucleophilic Functional Groups

In particular examples, the functionalized expanded porphyrins disclosed herein can be functionalized with linker moieties that comprise one or more nucleophilic functional groups. Such groups can react with one or more electrophilic groups on solid support to form a bond. It is understood that when a nucleophilic functional group is reacted with an electrophilic functional group, the nucleophilic functional group may no longer be nucleophilic. In this sense, the disclosed immobilized compositions can, in some examples, be without any nucleophilic functional groups on the expanded porphyrins; that is, the nucleophilic functional group has been coupled to an electrophilic functional group on the solid support and is no longer nucleophilic or, at least, as nucleophilic as before. However, for the purposes of this disclosure, various functional groups are identified in the immobilized expanded porphyrins by referring to them prior to bond formation.

Examples of nucleophilic functional groups that can be present on a functionalized expanded porphyrin include, but are not limited to, an amine, substituted amine, amide, substituted amide, hydroxyl, carboxylate, thiol, disulfide, azide, and alkoxide groups. In some aspects, one or more different nucleophilic groups can be present on the functionalized expanded porphyrin.

In one specific example, the nucleophilic functional group can be an amine or polymeric amine (i.e., a polymer that comprises one or more amine groups). In this instance, the amine can react with an electrophilic moiety on the solid support (e.g., reacting with an aldehyde or ester to form an imine or amide bond, respectively). The amine can also react with an isocyanate or thioisocyanate to form a urea or thiourea bond.

In another example, the polymeric amine can be an amino acid based polymer. As used herein "amino acid" means the typically encountered twenty amino acids which make up polypeptides. Suitable amino acid based polymers are "peptides," which are a class of compounds composed of amino acids chemically bound together. In general, the amino acids are chemically bound together via amide linkages (CONH); however, the amino acids can be bound together by other chemical bonds known in the art. For example, the amino acids can be bound by amine linkages. "Peptide" as used herein includes oligomers of amino acids and small and large peptides (e.g., proteins). Some specific examples of amino acid based polymers that are suitable for use a nucleophilic substituents on the disclosed functionalized expanded porphyrins include, but are not limited to, polylysine, proteins (e.g., enzymes), and peptides, including mixtures thereof.

Other suitable examples of polymeric amines are olefin based polymers that contain one or more amine functional group. Many such polyamines can be obtained commercially or can be prepared by methods known in the art. Suitable examples of polyamines that can used as a first active substance in the disclosed cellulose/active substance composites include, but are not limited to, polyvinyl amine and polyalkyleneimines like polyethyleneimine.

Still further examples of polymeric amines are polyamides that are prepared by the condensation of a diamine monomer with a diacid or diester monomer. Such polyamides are well known in the art and can be obtained commercially. Alternatively, polyamides can be prepared by self condensation of a monomer containing an amine and an acid or ester functional group, or through a ring opening reaction of a cyclic amide (i.e., lactam) such as caprolactam. Nylons are common examples of such polyamides.

Yet another example of a suitable polymeric amine is a polyether amine. Polyether amines contain primary amino groups attached to the terminus of a polyether backbone. The polyether backbone is typically based either on propylene oxide (PO), ethylene oxide (EO), or mixed EO/PO. In one aspect, the polyether amine can be a polyoxyalkyleneamines.

In yet another suitable example, the disclosed functionalized expanded porphyrins can be functionalized with an alcohol or polymeric alcohol (i.e., a polymer that comprises one or more hydroxyl groups). Similarly, thiols and polymeric thiols are suitable substituents. Such hydroxy and thiol groups can react with electrophilic groups on a solid support to form a bond (e.g., react with a halogen, aldehyde, ester, isocyanate, or thioisocyanate).

Electrophilic Functional Groups

In another aspect of the disclosed functionalized expanded porphyrins, the compounds can be functionalized with linker moieties that comprise one or more electrophilic functional groups that can react with a nucleophilic group on a solid support to form a bond. Examples of suitable electrophilic functional groups that can be used include, but are not limited to, aldehyde, carboxylic acid, acid anhydride, acid halide, ester (e.g., alkyl esters, activated carboxylic acid esters, thioester), halide, isocyanate, thioisocyanate, carbamate, carbonate, alkene, or alkyne groups. It is contemplated that one or more different electrophilic groups can be present on the first active substance.

In one example, the electrophilic functional group can be an ester, acid, polyester or a polyacid (i.e., a polymer that comprises one or more ester or acid groups, respectively). Polyesters and polyacids are well known and can be obtained commercially or by methods known in the art. Suitable examples of polyesters include, but are not limited to, polyalkylene terephthalates. Suitable examples of polymeric acids include, but are not limited to, poly(meth)acrylates and polymaleic acids, including mixtures and copolymers thereof.

Alkenes and alkynes are also suitable electrophiles, especially when adjacent to a carbonyl group. Such moieties react with nucleophiles like alcohols and amines via a Michael addition reaction to form ethers and amines, respectively.

Spacers

While the disclosed linker moiety can be attached to the expanded porphyrin directly, the use of a spacer, as is described herein, can allow more distance (and thus more freedom to move) between the expanded porphyrin and the solid support. The spacer can be of varying lengths, such as from 1 to 20 atoms in length. For example, the spacer can be from 1, 2, 3, 4, 5, 6, 7, 8, 9, 10, 11, 12, 13, 14, 15, 16, 17, 18, 19, or 20 atoms in length, where any of the stated values can form an upper and/or lower end point. As noted, the longer the spacer, the greater freedom of movement the expanded porphyrin can have. Further, the spacer can be substituted or unsubstituted. When substituted, the spacer can contain substituents attached to the backbone of the spacer or substituents embedded in the backbone of the spacer. For example, an amine substituted spacer can contain an amine group attached to the backbone of the spacer or a nitrogen in the backbone of the spacer. Suitable moieties for the spacer include, but are not limited to, substituted or unsubstituted, branched or unbranched, alkyl, alkenyl, or alkynyl groups, ethers, esters, polyethers, polyesters, polyalkylenes, polyamines, heteroatom substituted alkyl, alkenyl, or alkynyl groups, cycloalkyl groups, cycloalkenyl groups, heterocycloalkyl groups, heterocycloalkenyl groups, and the like, and derivatives thereof.

In one aspect, the spacer can comprise a $C_1$-$C_{10}$ branched or straight-chain alkyl, such as methyl, ethyl, n-propyl, iso-propyl, n-butyl, iso-butyl, sec-butyl, tert-butyl, n-pentyl, iso-pentyl, neopentyl, hexyl, heptyl, octyl, nonyl, or decyl. In a specific example, the spacer can comprise a $C_2$-$C_3$ alkyl, i.e., —$(CH_2)_n$—, wherein n is from 1 to 2. In another aspect, the spacer can comprise a $C_1$-$C_6$ branched or straight-chain alkoxy such as a methoxy, ethoxy, n-propoxy, iso-propoxy, n-butoxy, iso-butoxy, sec-butoxy, tert-butoxy, n-pent oxy, iso-pentoxy, neopentoxy, or hexoxy.

In still another aspect, the spacer can comprise a $C_2$-$C_6$ branched or straight-chain alkyl, wherein one or more of the carbon atoms is substituted with oxygen (e.g., an ether) or an amino group. For example, suitable spacers can include, but are not limited to, a methoxymethyl, methoxyethyl, methoxypropyl, methoxybutyl, ethoxymethyl, ethoxyethyl, ethoxypropyl, propoxymethyl, propoxyethyl, methylaminomethyl, methylaminoethyl, methylaminopropyl, methylaminobutyl, ethylaminomethyl, ethylaminoethyl, ethylaminopropyl, propylaminomethyl, propylaminoethyl, methoxymethoxymethyl, ethoxymethoxymethyl, methoxyethoxymethyl, methoxymethoxyethyl, and the like, and derivatives thereof. In one specific example, the spacer can comprise a methoxymethyl (i.e., —$CH_2$—O—$CH_2$—).

Solid Supports

Disclosed herein, in another aspect, are immobilized sensors that comprise one or more of the disclosed functionalized expanded porphyrins covalently attached to a solid support. Solid supports that can be used include, without limitation, silica gel, cellulose, glass, polymers, including polyacrylamide gel beads or polystyrene-poly(ethylene glycol) graft copolymer resins, and fiber optics. The solid support can be in a variety of sizes, shapes, and geometries, including flat surfaces, near-spherical beads, and thin fibers. Suitable solid supports can be obtain from commercial sources or synthesized by methods known in the art.

In many examples herein, the solid supports can be any of a range of naturally occurring or synthetic polymers, including, but not limited to, those used to make fiber optics, functionalized surfaces, or produce sensing beads and include, but are not limited to, cellulose, agorose, dextrose, acrylamide, glass slides, indium tin oxide, titanium oxide, control pore glass beads, polystyrene-polyethylene glycol resin, polystyrene-divinyl benzene resin, formylpolystyrene resin, tritylpolystyrene resin, acetyl polystyrene resin, chloroacetyl polystyrene resin, aminomethyl polystyrene-divinylbenzene resin, carboxypolystyrene resin, chloromethylated polystyrene-divinylbenzene resin, hydroxymethyl polystyrene-divinylbenzene resin, 2-chlorotrityl chloride polystyrene resin, 4-benzyloxy-2'4'-dimethoxybenzhydrol resin (Rink Acid resin), triphenyl methanol polystyrene resin, diphenylmethanol resin, benzhydrol resin, succinimidyl carbonate resin, p-nitrophenyl carbonate resin, imidazole carbonate resin, polyacrylamide resin, 4-sulfamylbenzoyl-4'-methylbenzhydrylamine-resin (Safety-catch resin), 2-amino-2-(2'-nitrophenyl) propionic acid-aminomethyl resin (ANP Resin), p-benzyloxybenzyl alcohol-divinylbenzene resin (Wang resin), p-methylbenzhydrylamine-divinylbenzene resin (MBHA resin), Fmoc-2,4-dimethoxy-4'-(carboxymethyloxy)-benzhydrylamine linked to resin (Knorr resin), 4-(2',4'-Dimethoxyphenyl-Fmoc-aminomethyl)-phenoxy resin (Rink resin), 4-hydroxymethyl-benzoyl-4'-methylbenzhydrylamine resin (HMBA-MBHA Resin), p-nitrobenzophenone oxime resin (Kaiser oxime resin), and amino-2,4-dimethoxy-4'-(carboxymethyloxy)-benzhydrylamine handle linked to 2-chlorotrityl resin (Knorr-2-chlorotrityl resin).

In some specific examples, the solid support can be any one of the various TENTAGEL™ resins from Rapp Polymere, Gmbh. These resins are grafted copolymers comprising a low crosslinked polystyrene matrix on which polyethylene glycol (PEG or POE) is grafted. As PEG and POE are "cameleon type" polymers with hydrophobic and hydrophilic properties, the graft copolymer shows modified physico-chemical properties. The copolymer typically contains from about 50 to about 70% PEG or POE (w/w). Therefore, the properties of these polymers are highly dominated by the properties of PEG or POE and no longer by the polystyrene matrix. TENTAGEL™ resins are available with various functional groups (nucleophilic and electrophilic) that can react with a suitable linker moiety to form a bond and thus immobilize the functionalized expanded porphyrins disclosed herein onto the TENTAGEL™ resin. For example, TENTAGEL™ resins with —C(O)H, —OH, —Br, —COOH, —SH, -Trityl, —O-methoxybenzyaldehyde, and —O-Ph-CH$_2$OH groups, to name but a few, with various alkyl and amide spacers, are available. One particularly suitable TENTAGEL™ resin contains a NH$_2$ functional group.

These solid supports, which are suitable for use herein, are commercially available or can be prepared by synthetic methods known in the art. The particular solid support chosen will depend primarily on the functional groups present on the expanded porphyrin.

Immobilization of the disclosed functionalized expanded porphyrins can be achieved by methods known in the art. For example, immobilization has been described in the case of other, non-actinide selective sensors to provide polymeric beads for use in, inter alia, array sensor systems, fiber optic probes, or test strips, wherein the molecular entity cannot wash off. See for example Goodey et al., *J Am Chem Soc* 123:2559-2570, 2001; Goodey i, *J Am Chem Soc* 125:2870-2871, 2003; Mcdevitt et al., International PCT Publication No. WO 2004/072613; and U.S. Pat. Nos. 6,602,702 and 6,680,206, which are incorporated in their entireties herein by reference. Also contemplated herein are methods where the pyrrole 3 (or any intermediates 7-10) is coupled to a solid support and then the expanded porphyrin is synthesized on the support in a manner like that of Schemes 1 and 2 supra.

EXAMPLES

The following examples are set forth below to illustrate the compositions, methods, and results according to the disclosed subject matter. These examples are not intended to be inclusive of all aspects of the subject matter disclosed herein, but rather to illustrate representative compositions, methods, and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Described in this example is the synthesis of an isoamethyrin with substituents in both the β-pyrrolic and bridging meso positions. Substitution at the latter sites can be used as a means of preparing functionalized isoamethyrins suitable for attachment to a solid support. As detailed below, the results of these efforts were systems that failed to function as receptors for the uranyl cation.

First, a bisphenyl hexapyrrin, a precursor in the synthesis of isoamethyrin, was synthesized. For this, the bisaryl bipyrrole (compound 27) was synthesized following published procedures (Bröring, *Synthesis* 9:1291-1294, 2000; Wallace et al., *J Org Chem* 58:7245-7257, 1993). Initially, attempts were made to synthesize a hexapyrrin from this precursor in accord with previously published procedures, as is shown in Scheme 5, Conditions 1 (Sessler et al., *J Chem Soc Chem Commun* 1289-1290, 1994). However, even with extended reaction times and/or heating the reaction mixture, only starting materials and decomposition products were observed. Thus, a procedure analogous to that used by Bröring in 2000 to prepare a bis-aryl substituted open chain tetrapyrrole was adopted (i.e., Scheme 5, Conditions 2) (Bröring, *Synthesis* 9:1291-1294, 2000). This produced hexapyrrin (compound 28) in 40% yield.

Scheme 5: Synthesis of isoamethyrin H$_2$2$^{2+}$•2Cl$^-$.

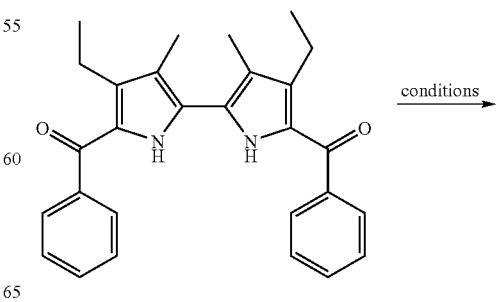

27

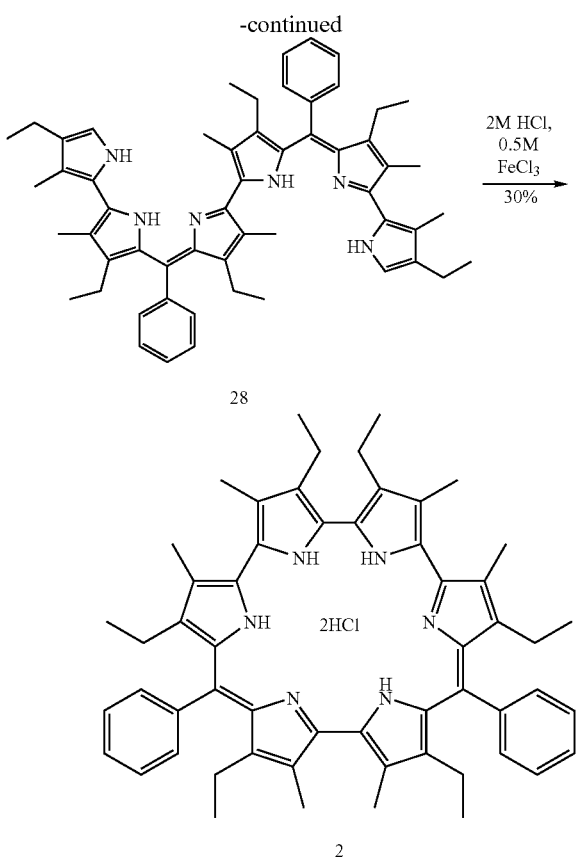

Conditions: 1) methanol, HCl (cat.); 2) POCl₃, heat, methanol, triethylamine 40%

With compound 28 in hand, an oxidative ring closing following the previously published procedure used to obtain the unfunctionalized isoamethyrin 1 was attempted in an effort to obtain the bis-phenyl substituted isoamethyrin 2 (Sessler et al., *Angew Chem Int Ed Engl* 40:591-594, 2001). Briefly, the hexapyrrin was dissolved in neat TFA and 1.2 equivalents of Na$_2$Cr$_2$O$_7$.2H$_2$O was added. Unfortunately, regardless of the reaction time employed, only decomposition products were observed.

At this juncture, oxidative ring closing with FeCl$_3$ were investigated. As disclosed in U.S. Pat. No. 6,984,734, which is incorporated in its entirety herein by reference, a series of cyclo[n]pyrrole macrocycles is obtained when bipyrroles such as compound 22 are stirred in a biphasic mixture of FeCl$_3$ in 1M HCl. Accordingly, a range of conditions were tested for the proposed Fe(III)-mediated oxidative ring closing of compound 28. Ultimately, it was found that stirring compound 28 in CH$_2$Cl$_2$ with 0.5 M FeCl$_3$ in 2 M HCl for 4-5 hours resulted in the best yield of compound 2, as monitored by TLC. Bis-phenyl isoamethyrin 2 was isolated in 30% yield after column chromatography over silica, a second column over alumina, and finally recrystallization from CH$_2$Cl$_2$/hexanes. It is assumed that the initial yield of the reaction was higher, but due to difficulties in purification, 30% is the highest isolated yield obtained to date.

Figure 8:
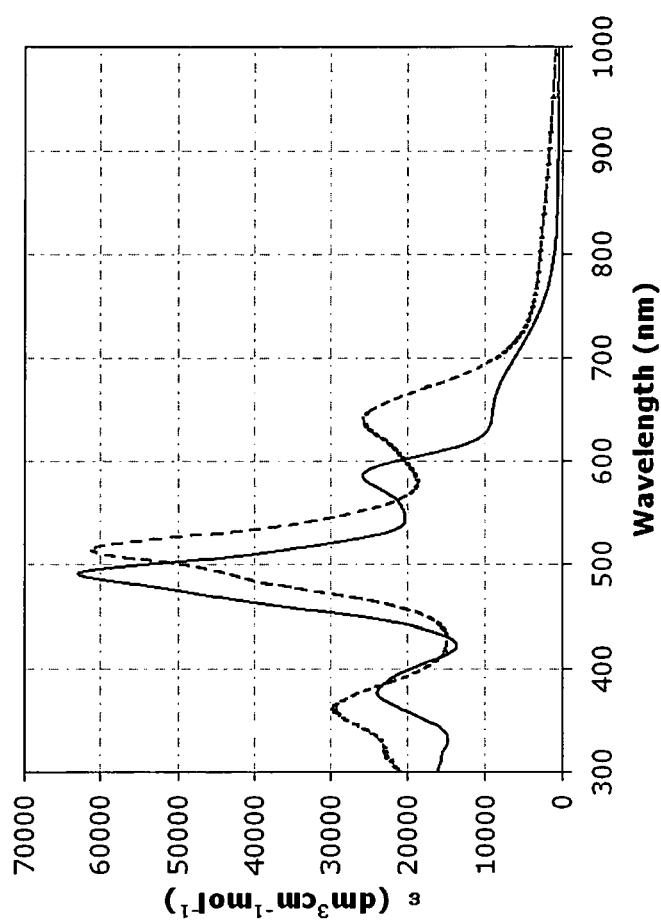
FIG. 8 is the UV-visible spectra of the bis-phenyl isoamethyrin 2 (dashed line), and unfunctionalized isoamethyrin 1 (solid line), as recorded in CH$_2$Cl$_2$.

FIG. 8 shows a side-by-side comparison of the UV-visible absorption spectra of compound 2 (dashed line) and isoamethyrin 1 (solid line). There is a slight red-shift of the Soret bands in the meso-aryl isoamethyrin; however, overall the shape of the spectra remains remarkably similar to that of isoamethyrin 1, providing support for the contention that the desired macrocycle (isoamethyrin 2), with identical conjugation to that present in isoamethyrin 1, was formed.

An $^1$H NMR spectroscopic comparison of the two macrocycles, however, reveals some important differences. The spectrum of the original aryl-free isoamethyrin 1 is characterized by NH proton signals at 23.66, 23.86, and 24.19 ppm, (500 MHz, CD$_2$Cl$_2$) due to the antiaromatic ring current of the expanded porphyrin. In the case of isoamethyrin 2, however, the corresponding NH peaks were observed at 14.15, 15.46, and 15.71 ppm (400 MHz, CDCl$_3$). While these values are shifted downfield compared to the NH signals of free pyrrole (about 7.5 ppm) and even the open chain hexapyrrin ($\delta$=11.45, 12.390 and 13.02 ppm), the shift is not as dramatic as that for isoamethyrin 1. Thus, it was concluded that significant distortion exists in isoamethyrin 2, and that the resulting deviations from planarity disrupt the conjugation pathway.

Figure 9:
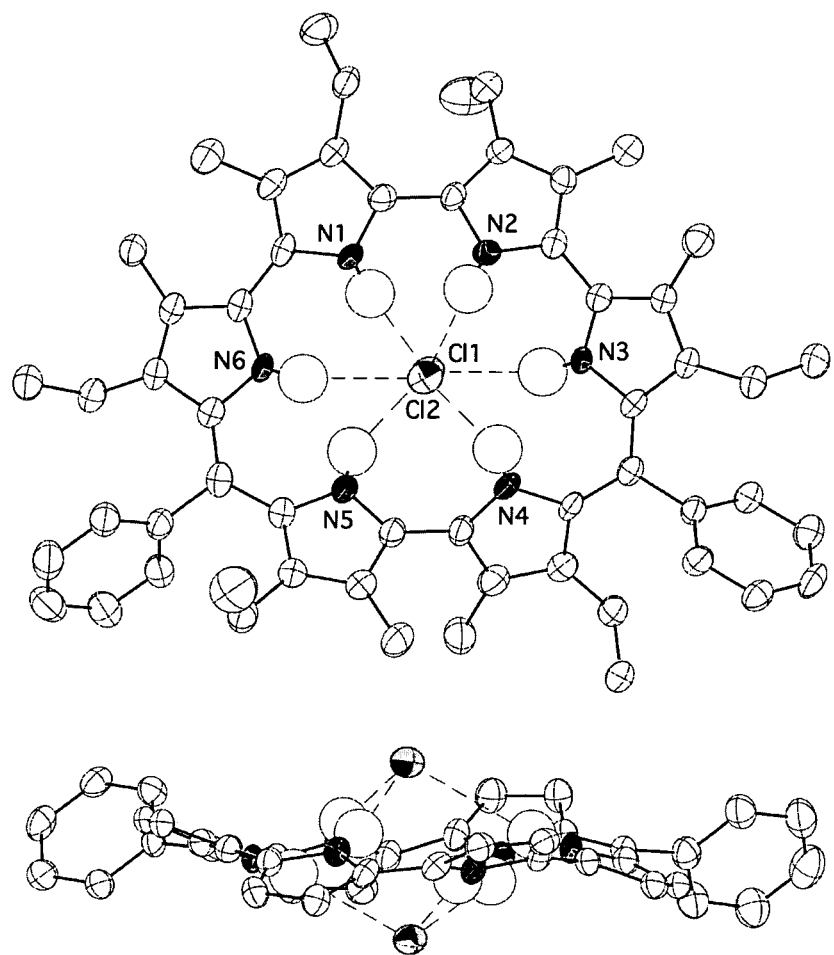
FIG. 9 is the crystal structure (front and side views) of bis-phenyl isoamethyrin H$_2$2$^{2+}$.2Cl$^-$ showing a partial atom labeling scheme. Most hydrogens, a molecule of THF, and the alkyl chains on the side view have been removed for clarity. Hydrogen bonds are indicated by dashed lines. Ellipsoids are scaled to the 50% probability level.
Figure 10:
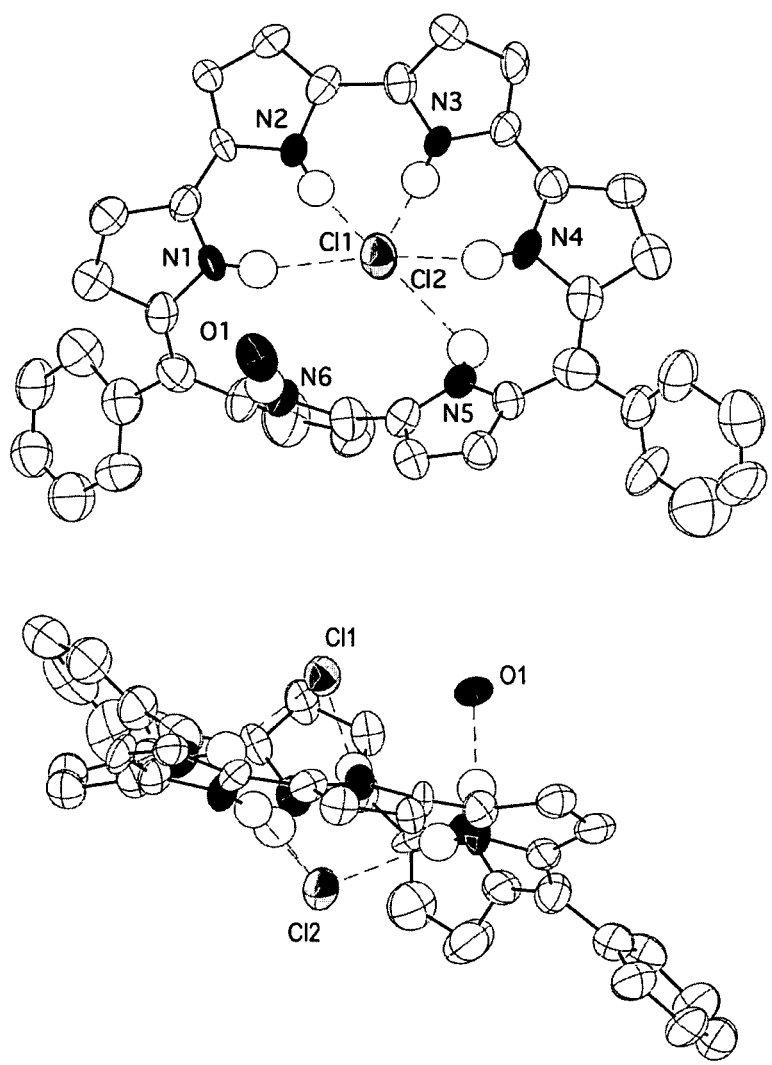
FIG. 10 is the crystal structure (front and side views) of bis-phenyl isoamethyrin H$_2$2$^{2+}$.2Cl$^-$ showing a partial atom labeling scheme and with a singular addition of one molecule of water hydrogen-bound to the N6 pyrrole NH. Most hydrogens, a molecule of THF, and the alkyl chains have been removed for clarity. Hydrogen bonds are indicated by dashed lines. Ellipsoids are scaled to the 50% probability level.

Structural proof for this assumption was provided by X-ray diffraction analysis, as shown in FIGS. 9 and 10. FIG. 9 displays front and side views of the bis-HCl salt of isoamethyrin 2. NH . . . Cl hydrogen bond distances range from 3.212 to 3.731 Å and are indicated by dashed lines. Overall, the molecule appears rather flat. The average dihedral angle in the quaterpyrrole unit is observed to be 139.8° and it is 118.0° in the bipyrrole unit (N5 and N4). However, the significant steric strain imposed by the two phenyl groups can be appreciated from the addition, and hydrogen bonding, of a molecule of water within crystal lattice of isoamethyrin 2. FIG. 10 shows the same bis-HCl salt of isoamethyrin 2 as was shown in FIG. 9 with the singular addition of one molecule of water hydrogen-bound (the N6-H . . . O distance is only 2.800 Å) to the N6 pyrrole NH. The remaining N—H hydrogen atoms are observed to form hydrogen bonds to one of the two chloride anions also present in the lattice, with an average N—H . . . Cl distance of 3.284 Å. The average dihedral angle in the quaterpyrrole is 147.2°, slightly higher that what was observed without the addition of the water molecule. However, the dihedral angle of the bipyrrole unit (N5 and N6) is now 72.4°.

$^1$H NMR spectroscopic studies were also used to obtain insights into the flexibility of isoamethyrin 2. For the spectra recorded in CD$_2$Cl$_2$ or CDCl$_3$, the triplet and quartet signals, corresponding to the β-ethyl groups, are relatively broad and are partial split into resonances that could be ascribed to individual, magnetically non-equivalent substituents. When an equivalent of D$_2$O is added to a solution of H$_2$2$^{2+}$.2Cl$^-$ in CDCl$_3$ (originally added to mimic conditions where water is H-bound to a pyrrolic NH), the peaks become further broadened. It can be concluded from this $^1$H NMR spectroscopic comparison that compound 2 is characterized by a relatively high degree of flexibility, leading to multiple conformers based on hydrogen-bonding interactions in aprotic solvents (when analyzed in CD$_3$OD, the $^1$H NMR spectra shows well-resolved peaks). These observations serve to confirm further that the antiaromatic ring current inherently present in the isoamethyrin ring system has been significantly weakened by the addition of the meso-phenyl moieties.

Figure 11:
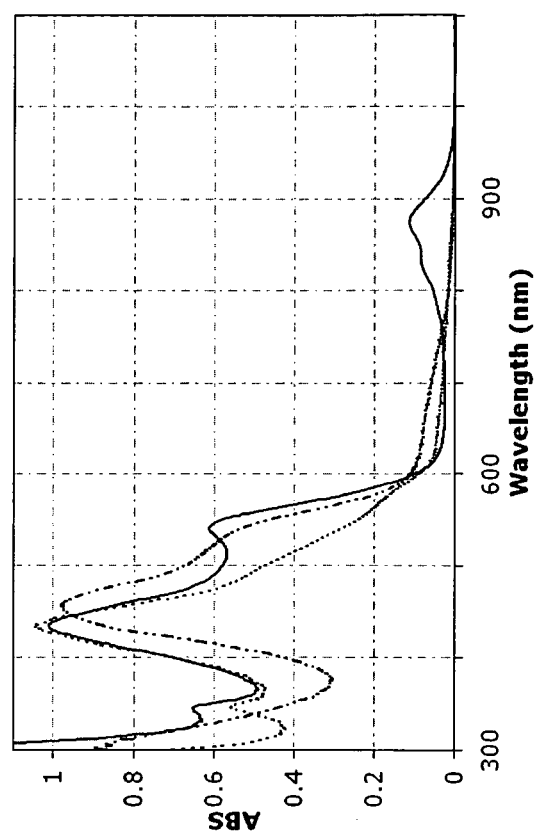
FIG. 11 is a graph showing the spectroscopic changes observed during the attempted metalation of isoamethyrin 2. The spectral traces shown are as follows: isoamethyrin 2 plus triethylamine (- . . . - . . . ); this same mixture with the addition of uranyl acetate and DDQ (solid line), and isoamethyrin 2 after being treated with triethylamine and DDQ ( - - - ).

Despite the significant steric hinderance observed in the solid state, the metalation of the meso-functionalized isoamethyrin 2 was investigated. The free base was obtained by washing with 10% aqueous NaOH a solution of H$_2$2$^{2+}$.2Cl$^-$. The free base was then dissolved in a mixture of CH$_2$Cl$_2$ and CH$_3$OH and uranyl acetate, dissolved in methanol, was added. The solution was stirred at room temperature for 24 hours while being periodically monitored by TLC and UV-Vis spectroscopy. However, no change in the spectrum ascribed to the starting material was observed (FIG. 11). It was presumed that ligand oxidation may be necessary for metal insertion, so DDQ was added to the reaction mixture. With this addition, a minor Q-like band was observed in the UV-visible spectrum (FIG. 11). Additionally, evidence for complex formation was also provided by mass spectrometry. However, attempts at purification led to retrieval of the starting free ligand. Therefore, it was concluded that meso-aryl substitution does not provide a fully effective means of generating functionalized isoamethyrin macrocycles suitable for attachment to solid supports. Contemplated herein, however, are meso-substituted isoamethyrin that are not substituted with aryl substituents but that are substituted with alkyl, ether, ester, amino, isocyanante, halide, or hydroxyl substituents.

9,18-Diphenyl-2,7,11,16,20,25-hexaethyl-3,6,12,15, 21,24-hexamethyl-hexapyrrin: (28)

Referring to Scheme 5, supra, phosphorus oxychloride (about 8 mL) was added to bipyrrole 27 (0.056 g, 0.132 mmol) under argon. The resulting red solution was then stirred at 60° for 0.5 hours. At this time, 2,2'-3,3'-dimethyl-4,4'-diethyl bipyrrole 11 (0.085 g, 0.39 mmol, 3 equivalents) was added and the now-purple mixture was stirred for an additional 3 hours. After cooling, the volatile components were removed using a rotary evaporator, leaving a green-blue residue, which was taken up in MeOH and $Et_3N$. This solution was stirred for 1 hour before the solvents were removed in vacuo. The resulting purple product was purified via column chromatography over silica gel (4% $CH_3OH$—$CH_2Cl_2$) with the fourth band, a purple/brown color, being isolated. Compound 28 was isolated as red crystals after recrystallization from $CH_2Cl_2$/hexanes (0.040 g, 34% yield). UV-vis, $CH_2Cl_2$: $\lambda_{max}$ nm ($dm^3mol^{-1}cm^{-1}$): 833 (8000), 561, (88000), 342 (25000). $^1$H NMR (400 MHz, $CDCl_3$): δ 0.765 (t, J=8 Hz, 6H, $CH_2CH_3$), 0.865 (t, J=8 Hz, 6H, $CH_2CH_3$), 1.037 (t, J=8 Hz, 6H, $CH_2CH_3$), 1.868-1.780 (m, 12H), 2.053 (s, 6H, $CH_3$) 2.116 (s, 6H, $CH_3$), 2.270 (q, J=8 Hz, 8H, $CH_2CH_3$), 2.309 (s, 6H, $CH_3$), 6.405 (s, 2H, CH), 7.544-7.471 (m, 10H, $C_6H_5$), 11.450 (s, 2H, NH), 12.390 (s, 2H, NH), 13.019 (s, 2H, NH). $^{13}$C (100 MHz, $CDCl_3$): δ 10.8, 11.0, 11.3, 14.1, 15.3, 15.6, 18.5, 19.1, 39.4, 116.2, 119.0, 122.9, 124.355, 127.0, 127.6, 127.9, 128.2, 129.9, 134.0, 136.0, 137.1, 138.1, 140.0, 142.2, 146.5, 153.1. HRMS ($ESI^+$) m/e calc'd. for $C_{56}H_{65}N_6$ $(M^{+1})^+$: 821.527072. found: 821.525929.

Bisphenyl-isoamethyrin, 2

Hexapyrrin 28 (0.062 g, 0.0693 mmol) was dissolved in 10 mL $CH_2Cl_2$. To this solution, 4 mL of 0.5 M $FeCl_3$ in 2 M HCl was added dropwise and the reaction was allowed to stir at room temperature for 3-5 hours, or until judged complete by TLC analysis. The biphasic mixture was then separated and the organic layer was washed with water (3×100 mL), saturated $NaHCO_3$ (2×100 mL) and 1 M HCl (2×100 mL). The organic layer was then dried over sodium sulfate and the solvent removed in vacuo. The residue was then columned over silica with 2% $MeOH/CH_2Cl_2$ as the elutant. The purple/red spot was isolated and concentrated. The residue was then subject to column chromatography using alumina as the solid support and with 1:1 (v/v) EtOAc:Hexanes as the eluent. The red/orange band was isolated and the solvent was removed in vacuo. The residue was washed with 1M HCl (2×50 mL), dried over sodium sulfate, and concentrated before being recrystallized from $CH_2Cl_2$/hexanes. Compound 2 was isolated in the form of purple crystals purple crystals. (0.010 g, 16% yield). Crystals suitable for X-ray diffraction were grown from slow evaporation of a THF/cyclohexane mixture. UV-visible: $\lambda_{max}$ ($CH_2Cl_2$)/nm 364 (ε/$dm^3mol^{-1}cm^{-}$ 27000), 515 (63500), 642 (23500). $^1$H NMR (400 MHz, $CDCl_3$): δ 0.677 (m, 12H), 1.030 (t, J=8 Hz 6H, $CH_2CH_3$), 1.459 (s, 6H, $CH_3$), 1.802 (s, 12H, $CH_3$, $CH_3$), 2.195 (m, 4H), 2.293 (m, 4H), 7.487-7.154 (m, 10H, $C_6H_5$), 14.153 (s, 2H, NH), 15.460 (s, 2H, NH), 15.713 (s, 2H, NH). $^{13}$C NMR (100 MHz, $CDCl_3$): δ 7.6, 10.2, 10.4, 13.1, 13.3, 13.9, 17.1, 18.5, 18.5, 28.7, 35.6, 121.2, 126.2, 127.0, 127.2, 127.5, 129.6, 129.9, 130.0, 130.1, 130.4, 131.9, 134.2, 135.7, 136.3, 137.7, 149.7, 150.1, 150.5. HRMS (ESI+H) m/z calc'd. for $C_{56}H_{63}N_6$: 819.511422. found: 819.512411.

Example 2

Described in this example is the synthesis of isoamethyrin expanded porphyrins functionalized with substituents in the β-pyrrolic positions that render this macrocycle suitable for attachment to a solid support. Also detailed in this example is the attachment of the acid functionalized isoamethyrin 14 to a tentagel bead.

The synthesis of functionalized isoamethyrins 13-15 is based on the known bipyrrole 9 described by Jeong Tae Lee as shown in Scheme 1, supra (Lee, "Cyclo[n]pyrroles and Their Applications," Ph.D. Dissertation, The University of Texas at Austin, May, 2006). Bipyrrole 9 was formylated in moderate yields using a modification of the Vilsmeier-Haack reaction to give the diformyl bipyrrole 10. With the resulting diformyl precursor 10 in hand, the open chain hexapyrrin 12 could be prepared by condensing one equivalent of the diformyl precursor 10 with 2 equivalents of the unfunctionalized (albeit alkyl substituted) bipyrrole 11 in the presence of catalytic HCl, as is shown in Scheme 2, supra. Applying similar oxidative-ring closing procedures, as were used to generate compound 2, allowed isoamethyrin 13 to be synthesized in 16% yield.

Figure 12:
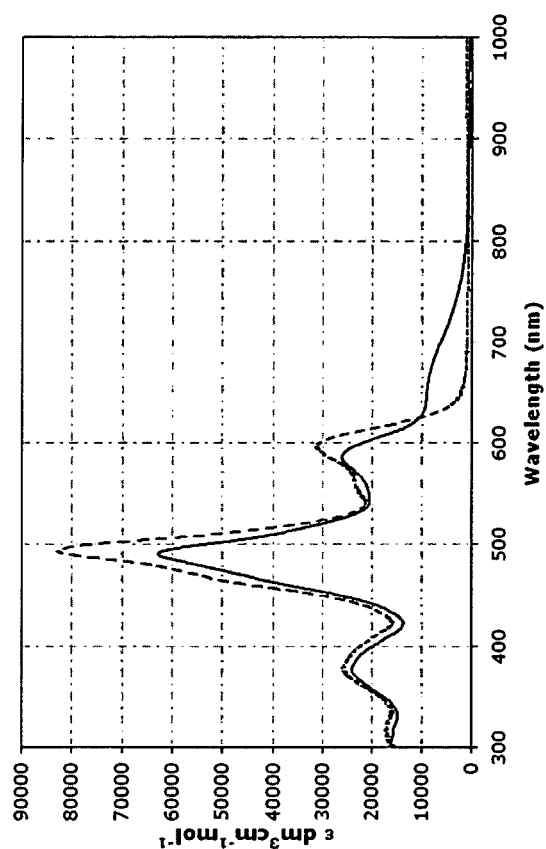
FIG. 12 is the UV-visible spectra recorded in CH$_2$Cl$_2$ for isoamethyrin H$_2$12$^+$.2Cl$^-$ (solid line) and H$_2$13$^{2+}$.2Cl$_-$ (dashed line).

The UV-visible spectrum (FIG. 12) of $H_213^{2+}.2Cl^-$ (solid line) is similar to that of isoamethyrin $H_21^{2+}.2Cl^-$ (dashed line) with one major difference: it shows an increased extinction coefficient of nearly 20000 $dm^3$ $cm^{-1}mol^{-1}$. In spite of these differences, these UV-visible spectral results were considered consistent with the fact that the functionalized isoamethyrin 13 had indeed been prepared and successfully converted to its diprotonated salt. This latter transformation was effected by treating the free-base form with HCl.

Figure 13:
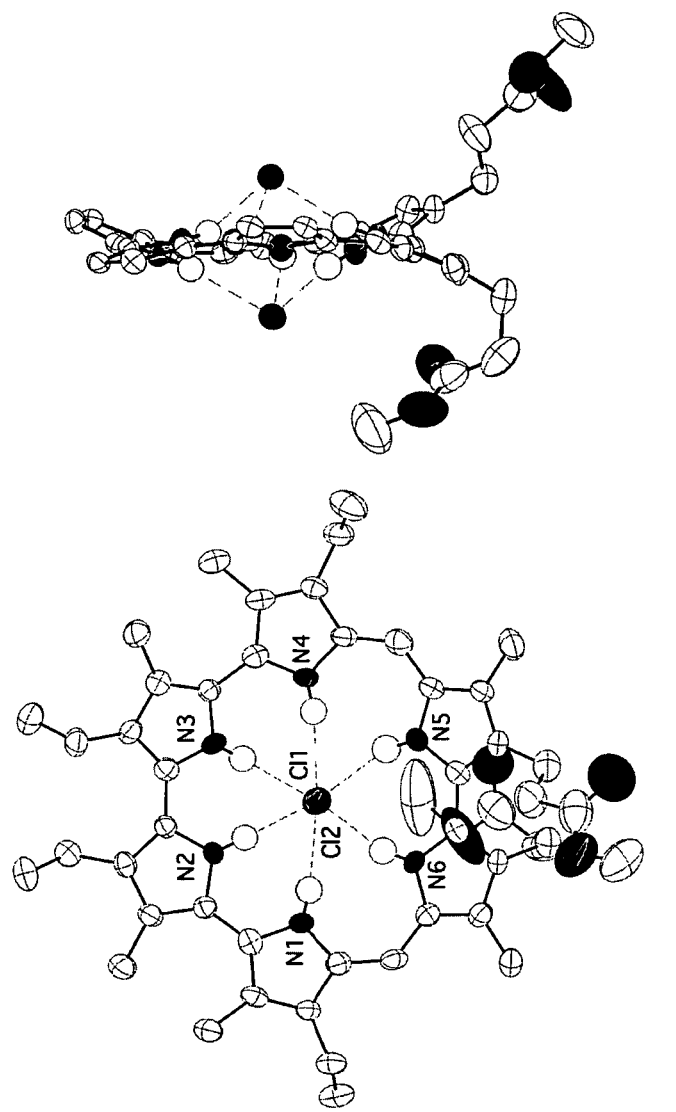
FIG. 13 is the crystal structure (top and side views) of the bis-HCl salt of isoamethyrin 13 showing a partial atom labeling scheme. Most hydrogen atoms and the alkyl substituents on the side view have been removed for clarity. Ellipsoids are scaled to the 50% probability level.

Crystals suitable for single-crystal X-ray analysis were grown from slow evaporation of a $CH_2Cl_2$/hexanes mixture and the resulting structure is shown in FIG. 13. As was true for isoamethyrin 1, the new functionalized derivative 13 could be made to crystallize in the form of its bis-chloride salt. As can be seen from inspection of FIG. 13, the core of the macrocycle is essentially planar. This is true in spite of the fact that the methyl ester groups point out as far from each other as possible. All six nitrogens participate in hydrogen-bonding interactions with one of the two chloride anions as inferred from the N—H . . . Cl distances, which range from 2.380 to 2.753 Å. The six pyrroles are observed to adopt a slight up-down conformation with deviations from the plane defined by the six pyrrolic nitrogens ranging from 0.123 to 0.169 Å.

Figure 14:
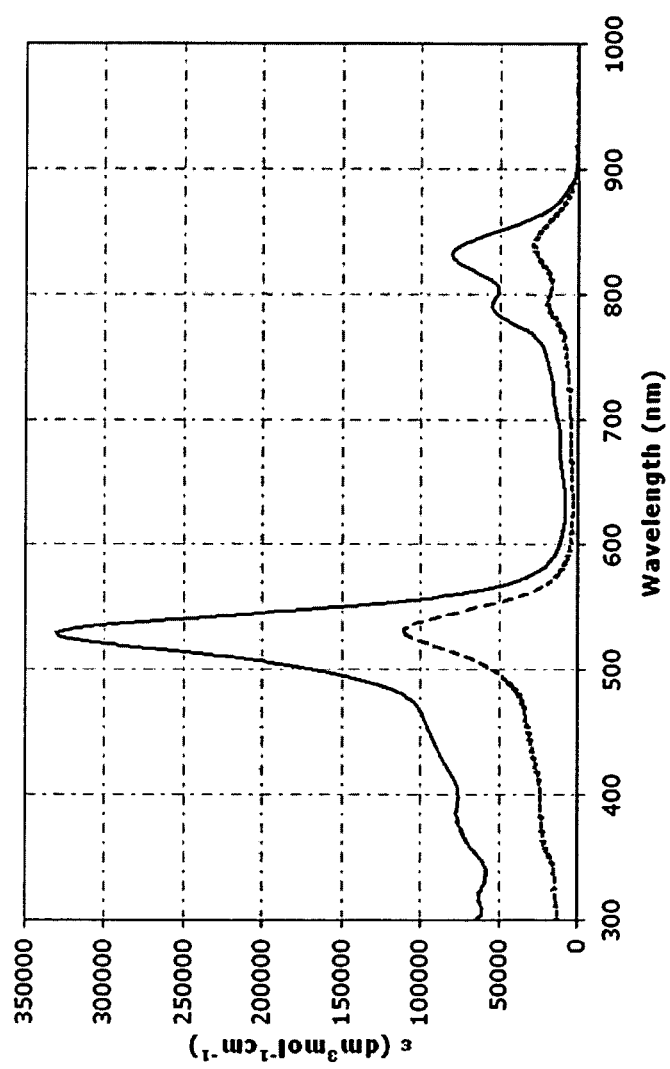
FIG. 14 is a graph showing a comparison of extinction coefficients and UV-visible spectra recorded in CH$_2$Cl$_2$ for UO$_2$.isoamethyrin 1 (solid line) and UO$_2$.isoamethyrin 13 (dashed line).

Prior to immobilizing compound 13 and its derivatives onto solid supports, tests were made to determine the effect (if any) the synthetic attachment of the methyl ester groups had on the interactions of the macrocycle with uranyl cations. Towards this end, the free base form of compound 13 was dissolved in a dichloromethane-methanol mixture and 2 equivalents of uranyl acetate, dissolved in methanol, were added. Formation of the uranyl-isoamethyrin complex was monitored by TLC over the course of two days, at which time complex formation was deemed complete. The $^1$H NMR shifts seen in comparing the spectra of compound 13 and its uranyl complex mirrors that observed for isoamethyrin 1 and its uranyl complex. This spectral analogy leads to the conclusion that, like isoamethyrin 1, compound 13 undergoes oxidation concurrent with metal coordination, thereby producing an aromatic species. The UV-visible spectrum (FIG. 14), of compound 13.$UO_2$ recorded in $CH_2Cl_2$ (solid line), revealed the growth of a Q-like band that bears analogy to what is seen during the formation of the uranyl complex of isoamethyrin 1 (dashed line). However, the calculated extinction coefficients for the $UO_2$ complex of compound 13.$UO_2$ were found to be ⅓ that of isoamethyrin 1.$UO_2$. Nonetheless, the spectral changes could be easily monitored by the naked eye, meaning that compound 13 retained its critical utility as a spectrometric actinide cation sensor.

Figure 15:
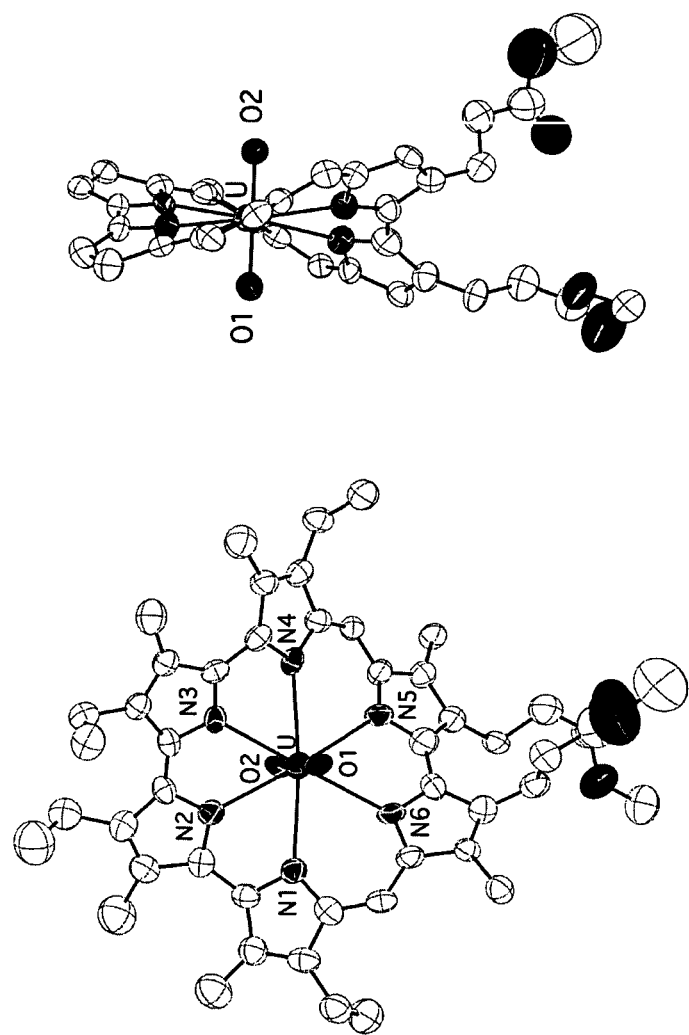
FIG. 15 is a crystal structure (top and side views) of UO$_2$.isoamethyrin 13 showing a partial atom labeling scheme. Ellipsoids are scaled to the 50% probability level. All hydrogen atoms and the alkyl substituents in the side view have been removed for clarity.

Inspection of the crystal structure of $UO_2$.with compound 13 (FIG. 15) reveals that the uranyl cation sits within the plane of the macrocycle and as expected, is coordinated to two trans oxo ligands and all six nitrogen atoms of compound 13. Three molecules of the $UO_2$-13 complex are present in the unit cell. However, minimal differences, namely placement of the β-substituents, are observed between the three molecules. Additionally, minor differences between the U—O bond lengths, which range from 1.736(9) to 1.7730(6) Å were observed between the three molecules in the unit cell. The average U—N bond distance is 2.641(5) Å, and the U—N bond angles range from 64.85 to 58.30°. Both values are similar to that reported for $UO_2$.with isoamethyrin 1. These crystallographic data lead to the conclusion that the additional methyl ester groups do not interfere with uranyl cation coordination in the case of isoamethyrin 13. As such, efforts were made to immobilize 13 or one of its derivatives onto a solid support. Such covalent attachments were successfully carried out in the case of so-called tentagel beads using literature procedures (Goodey et al., *J Am Chem Soc* 123:2559-2570, 2001; Goodey et al., *J Am Chem Soc* 125:2870-2871, 2003).

With isoamethyrin 13 in hand, modification of the methyl ester moieties to carboxylic acid and alcohol groups was effected (Scheme 2, supra). Macrocycle 14 was formed following a procedure established for the hydrolysis of methyl ester moieties appended on pentaphyrin(1.1.1.1.0) (Kral et al., *J Med Chem* 45:1073-1078, 2002). Specifically, hydrolysis of compound 13 was effected in good yields by stirring the macrocycle in neat TFA and concentrated HCl for 15 to 20 minutes. The diacid 14 was then purified through column chromatography over silica and using 10% methanol in chloroform as the eluent as shown in Scheme 2.

Further referring to Scheme 2, the diol 15 was also synthesized from the methyl ester 13. After attempts at reduction using $BH_3$ and LAH, which resulted in isolation of the starting material, reduction with (di-isobutyl aluminum hydride) DiBAlH was found to be more effective; this gave the desired diol in isolated yields of just over 20%.

Diformyl bipyrrole 10

Referring to Scheme 1, supra, 2.14 mL of $POCl_3$ was added dropwise to 3 mL DMF at 0° C. under argon. The resulting mixture was then stirred at room temperature for 10 minutes and then cooled back down to 0° C. A solution of compound 9 (0.3811 g, 1.76 mmol) in a minimal amount of DMF (about 2 mL) was then slowly added over the course of 10 minutes while covered from light. Once addition was complete, the reaction mixture was warmed to room temperature and stirred in the dark for 2 hours. After this, 100 equivalents of $NaCO_3$ (12.19 g) and 1 mL of MeOH was slowly added to the mixture. The reaction mixture was stirred for an additional hour. An excess of water was added to the solution, turning the green solution to yellow. The mixture was stirred for an additional 3 hours before filtering off the solution and washing the solid with an excess of water (0.1459 g, 21%). $^1$H NMR (400 MHz, $CDCl_3$): δ 2.370 (s, 6H, $CH_3$), 2.821-2.799 (m, 8H, $CH_2CH_2$), 3.696, (s, 6H, $COCH_3$), 9.714 (s, 2H, CHO), 11.650, (s, 2H, NH). $^{13}$C (100 MHz, $CDCl_3$): δ 9.3, 19.0, 29.6, 32.8, 52.3, 121.5, 128.1, 130.0, 175.3. HRMS ($CI^+$) m/e calc'd. for $C_{20}H_{25}N_2O_6$ ($M^{+1}$)$^+$: 389.171262. found: 389.172425.

2,7,20,25-tetraethyl-3,6,11,16,21,24-hexamethyl-12,15-di-ethylmethylester) hexapyrrin, 12

Diformyl bipyrrole 10 (0.159 g, 0.409 mmol) was dissolved in approximately 700 mL of methanol and heated to 60° C. Once the solid was completely dissolved, 0.195 g (0.901 mmol, 2.2 equivalents) of methyl ethyl bipyrrole 11 was added in two aliquots. In the first aliquot, 0.8 equivalents, 0.07 g was added to the solution followed by 4 drops of concentrated HCl. The solution was stirred for 5 minutes and the remaining bipyrrole was added (about 0.125 g). The solution stirred for approximately 20 hours at 60° C. At this point, the methanol was removed in vacuo and the purple-red solid was recrystallized from $CH_2Cl_2$/hexanes to give compound 12 as a red solid (0.199 g; 57% yield). UV-visible: $\lambda_{max}$ ($CH_2Cl_2$)/nm 525 (ε/$dm^3 mol^{-1} cm^{-1}$ 98000), 752 (25000), 434 (22000). $^1$H NMR (400 MHz, $CDCl_3$): δ 1.096 (t, J=7.6, 6H, $CH_2CH_3$), 1.272 (t, J=7.4 Hz, 6H, $CH_2CH_3$), 2.200 (s, 6H, $CH_3$), 2.216, (s, 6H, $CH_3$), 2.399-2.370 (m, 10H, $CH_3$ and $CH_2CH_3$), 2.546 (t, J=8.2 Hz, 2H, $CH_2CH_2$), 2.764 (q, J=8 Hz, 2H, $CH_2CH_3$), 2.991 (t, J=8 Hz, 2H, $CH_2CH_2$), 3.589 (s, 6H, $COCH_3$), 6.318 (s, 2H, py-H), 7.097 (s, 2H, CH), 11.625 (s, 4H, NH), 12.527 (s, 2H, NH). $^{13}$C NMR (75 MHz, $CDCl_3$): δ 10.9, 12.4, 13.0, 14.3, 15.8, 18.9, 19.0, 21.3, 34.2, 52.0, 115.2, 120.1, 124.3, 125.3, 126.0, 127.0, 129.2, 129.5, 131.7, 135.3, 136.9, 150.8, 151.2, 173.5. HRMS ($ESI^+$) m/e calc'd. for $C_{48}H_{61}N_6O_4$ ($M^+$): 785.47566. found: 785.47488.

Isoamethyrin dimethyl ester, 13

Intermediate 12 (0.183 g, 0.21 mmol) was dissolved in 20 mL $CH_2Cl_2$. A solution containing 10 mL of 0.5 M $FeCl_3$ in 2M HCl was added and the biphasic mixture was stirred for 4 hours or until judged complete by TLC (8% $CH_3OH$ in $CH_2Cl_2$, eluent). The layers were then separated and the organic layer was washed several times with water (3×100 mL) and 1 M HCl (2×100 mL) before being dried over sodium sulfate and dried in vacuo. The resulting solid was purified by column chromatography over silica gel using 2-5% $CH_3OH/CH_2Cl_2$ as the eluent. The first red fraction (major product) was collected. This fraction was concentrated in vacuo and washed with 1 M HCl, dried over $Na_2SO_4$, and again dried in vacuo. Recrystallization from $CH_2Cl_2$ layered with hexanes afforded compound 13 in the form of green crystals with a metallic luster (0.0734 g, 40% yield). UV-visible ($CH_2Cl_2$)/nm: $\lambda_{max}$ 378 (ε/$dm^3 mol^{-1} cm^{-1}$/24600), 494 (81 100), 596 (32 500). $^1$H NMR (400 MHz, $CDCl_3$): δ 0.497 (t, J=7.4 Hz, 6H, $CH_2CH_3$), 0.622 (t, J=7.4 Hz, 6H, $CH_2CH_3$), 0.900 (s, 6H, $CH_3$), 1.039 (s, 6H, $CH_3$), 1.125 (s, 6H, $CH_3$), 1.410-1.342 (m, 8H), 1.484 (t, J=7.4 Hz, 4H, $CH_2CH_2$), 2.281 (t, J=8 Hz, 4H, $CH_2CH_2$), 3.582 (s, 2H CH), 3.919 (s, 6H, $COCH_3$), 22.689 (s, 2H, NH), 23.088 (s, 2H, NH), 23.340 (s, 2H, NH). $^{13}$C NMR (75 MHz, $CDCl_3$): δ 9.3, 9.5, 10.7, 13.0, 13.9, 16.4, 16.9, 19.3, 33.0, 52.1, 118.8, 123.8, 126.1, 131.6, 131.8, 132.3, 132.7, 135.0, 137.6, 138.1, 141.6, 151.6, 157.8, 173.0. HRMS (ESI$^+$) m/e calc'd. for $C_{48}H_{59}N_6O_4$ (M$^+$): 783.456. found: 783.45923.

$UO_2$-13

The "free base" form of isoamethyrin 13 (0.012 g, 1.5 mmol) was dissolved in a 50:50 v/v mixture of $CH_2Cl_2$/$CH_3OH$. A solution of uranyl acetate (0.0082 g, 1.9 mmol, 1.2 equiv) dissolved in $CH_3OH$ was added and the solution was allowed to stir overnight. At this point, the solvent was removed in vacuo and the residue was taken up in $CH_2Cl_2$. The product was purified by column chromatography (neutral alumina, 50-200 μm) using a 2:3 v/v mixture of ethyl acetate/hexanes as the eluent. The first red band was isolated and the solvent was removed in vacuo. The solid was recrystallized from $CH_2Cl_2$/hexanes to give 0.0037 g of metallic green crystals of $UO_2$-13 (24%). UV-visible ($CH_2Cl_2$)/nm: $\lambda_{max}$ 531 (ε: $dm^3 cm^{-1} mol^{-1}$ 98000), 839 (24 000), 793 (17 000). $^1$H NMR (500 MHz, $CDCl_3$): δ 1.823-1.912 (m, 6H, $CH_2CH_3$), 2.805 (t, J=8.33, $CH_2CH_2COOCH_3$), 3.373 (s, 12H, $CH_3$), 3.581 (s, 6H, $CH_3$), 3.662 (s, 6H, $CH_3$), 4.043 (q, J=7.40, 4H, $CH_2CH_3$), 4.082 (q, J=7.38, 4H, $CH_2CH_3$), 4.329 (t, 4H, $CH_2CH_2COOCH_3$), 9.926 (s, 2H, meso-H). $^{13}$C (125 MHz, $CDCl_3$): δ 12.3, 15.9, 16.5, 17.1, 18.0, 20.1, 21.3, 24.1, 36.0, 51.5, 107.6, 134.9, 136.6, 138.3, 144.3, 145.3, 145.6, 147.3, 148.0, 148.6, 149.4, 151.3, 151.5. HRMS (ESI$^+$) m/e calc'd. for $C_{48}H_{55}N_6O_6U$ (M$^+$): 1049.4691. found: 1049.4683.

Diacid isoamethyrin, 14

Isoamethyrin diester 13 (0.1221 g, 0.143 mmol) was placed in a 2-neck round bottom flask under argon. A solution of 5.5 mL fresh TFA and 5.5 mL concentrated HCl were added to the flask and the reaction was stirred for 24 hours. At this point, about 150 mL $H_2O$ was added and the product was extracted from $CH_2Cl_2$. The organic layers were combined, washed with 1M HCl, and dried over $Na_2SO_4$. The solid was then purified by column chromatography over silica gel and 10% $CH_3OH$/$CH_2Cl_2$ as the eluent, until the majority of impurities were removed. 0.1% TFA was then added to the eluent and the orange-red band was collected (0.1181 g 85% yield). UV-visible: $\lambda_{max}$ ($CH_2Cl_2$)/nm 377 (ε/$dm^3 mol^{-1} cm^{-1}$ 18500), 497 (57000), 599 (22500). $^1$H NMR (400 MHz, $CDCl_3$): δ 0.496 (t, J=7 Hz, 6H, $CH_2CH_3$), 0.647 (t, J=7.6 Hz, 6H, $CH_2CH_3$), 0.948 (s, 6H, $CH_3$), 1.055 (s, 6H, $CH_3$), 1.216 (s, 6H, $CH_3$), 1.406 (br-m, 8H, $CH_2CH_3$), 1.601 (br-t, 4H, $CH_2CH_2$), 2.376 (br-t, 4H, $CH_2COOH$), 3.712 (s, 2H, CH), 8.150, 22.207 (s, 2H, NH), 22.620 (s, 2H, NH), 22.891 (s, 2H, NH). HRMS (ESI$^+$): m/e calc'd. for $C_{46}H_{55}N_6O_4$ (M$^+$): 755.4289. found: 755.42793.

Dihydroxy Isoamethyrin, 15

1.5 M DiBAlH (0.91 mL) in toluene was added to a flame-dried 2-neck RBF with 1 mL of dry toluene at 0° C. under argon. The free base form of diester 13 (0.0763, 0.0975 mmol), previously dissolved in 20 mL of dry toluene, was added dropwise. The solution was kept at 0° C. for 0.5 hours and then water (about 1 mL), followed by 10% NaOH (about 2 mL), was added to the solution and it was stirred for a further 20 minutes. At this time, $CH_2Cl_2$ (50 mL) was added to the mixture and the organic layer was separated. It was then washed with water (2×50 mL) and 1M HCl (2×50 mL). The organic layer was collected, dried over sodium sulfate, and the solvent was removed in vacuo. The resulting purple residue was then subjected to purification via column chromatography over silica gel using 2% $CH_3OH$/$CH_2Cl_2$ as the eluent. The third band, a brown/red fraction, was collected and the solvent was removed. The residue was then redissolved in $CH_2Cl_2$ and washed with 1M HCl (2×50 mL). The resulting solution was dried over anhydrous $Na_2SO_4$, concentrated to about 2 mL, and layered with hexanes. After cooling overnight, a purple solid, corresponding to compound 15, formed; it was collected and dried to give 0.0167 g (22% yield). UV-visible: $\lambda_{max}$ ($CH_2Cl_2$)/nm 379 (ε/$dm^3mol^{-1}cm^{-1}$ 19000), 498 (61000), 598 (23500). $^1$H NMR (400 MHz, $CDCl_3$): δ 0.522 (t, J=7.2 Hz, 6H, $CH_2CH_3$), 0.662 (t, J=7.2 Hz, 6H, $CH_2CH_3$), 0.961 (s, 6H, $CH_3$), 1.066 (s, 6H, $CH_3$), 1.213 (s, 6H, $CH_3$), 1.446-1.372 (m, 12H), 1.595 (5-et, J=6.4 Hz, 2H, $CH_2CH_2CH_2$), 3.767 (s, 2H, CH), 4.076 (t, J=6.4 Hz, 4H, $CH_2OH$), 22.068 (s, 2H, NH), 22.552 (s, 2H, NH), 22.900 (s, 2H, NH). $^{13}$C-NMR (75.4 MHz, $CD_2Cl_2$): δ 9.6, 9.9, 10.9, 13.3, 14.1, 16.8, 17.4, 20.5, 31.8, 61.8, 119.8, 123.8, 126.6, 131.6 (2 peaks), 132.6, 134.1, 135.4, 137.3, 139.2, 142.9, 152.3, 157.1. HRMS (ESI$^+$): m/z calc'd for $C_{46}H_{59}N_6O_2$ (M$^{+H)}$: 727.4688. found: 727.46940.

Example 3

Immobilization of Compound 14 onto a TG-$NH_2$ Functionalized Bead

Four batches of beads, weighing 0.0065 g, 0.0061 g, 0.0071 g, and 0.006 g, respectively, were initially "activated" by shaking them in a solution containing DMF and 10 equivalents of N,N-diisopropyl amine (DiPEA). After 30 minutes, the solution was removed and the beads were washed with DMF. The beads were then re-suspended in a solution containing DMF, 4 equivalents of DiPEA, 1.9 equivalents of PyBOP and $\frac{1}{25}^{th}$, $\frac{1}{20}^{th}$, $\frac{1}{15}^{th}$, and $\frac{1}{10}^{th}$ equivalents (7.8×10$^{-8}$ mol, 9.15×10$^{-8}$ mol, 1.42×10$^{-7}$ mol, and 1.92×10$^{-7}$ mol, respectively) of compound 14. The suspension was shaken until the DMF solution had lost its pigmentation (about 6 hours). The beads were then washed repeatedly with 1 M HCl (aq) and 1 M NaOH (aq) to remove the PyBOP and DMF. Evidence for successful attachment was provided by the observation of color changes upon exposure to the uranyl cation.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the formula:

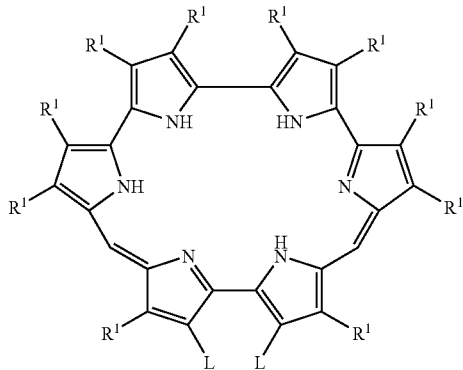

wherein each $R^1$ is, independent of the others, hydrogen, a substituted or unsubstituted alkyl, cycloalkyl, alkoxy, alkenyl, cycloalkenyl, alkynyl, cycloalkynyl, or aryl; and wherein each L is, independent of the other, alkyl oxycarbonyl, carboxy or salt thereof, halocarbonyl, alkyl thiocarbonyl, hydroxy, amino, substituted amino, carbamoyl, substituted carbamoyl, azido, isocyano, thioisocyanato, sulfanyl, disulfanyl, halide, alkoxy, substituted alkoxy, acylamino, alkenyl, alkynyl, or anhydride group, wherein each L is attached to the compound directly or wherein each L is attached to the compound by a spacer of from 1-20 atoms in length.

2. The compound of claim 1, wherein each $R^1$ is, independent of the others, methyl or ethyl.

3. The compound of claim 1, wherein $R^1$ is heteroaryl.

4. The compound of claim 1, wherein each L, independent of the other, is —CH$_2$CH$_2$CO$_2$CH$_3$, —CH$_2$CH$_2$CO$_2$H, or —CH$_2$CH$_2$CH$_2$OH.

5. The compound of claim 1, wherein the spacer is a $C_1$-$C_{10}$ branched or straight-chain alkyl.

6. The compound of claim 1, wherein the spacer is a $C_2$-$C_3$ alkyl.

7. The compound of claim 1, wherein L is a hydroxy, methyl oxycarbonyl, or carboxy or salt thereof attached to the compound by a $C_2$-$C_3$ alkyl spacer.

8. The compound of claim 1, wherein the compound has the formula:

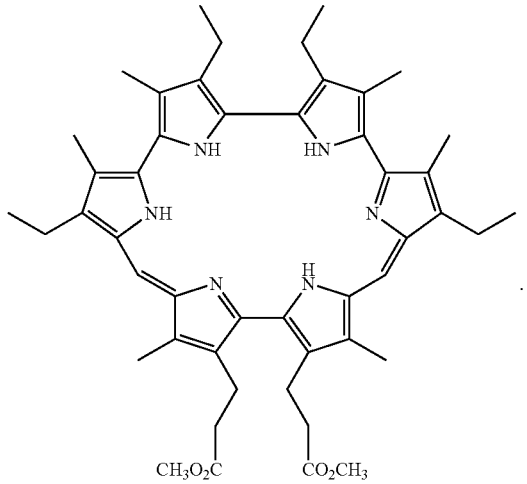

9. The compound of claim 1, wherein the compound has the formula:

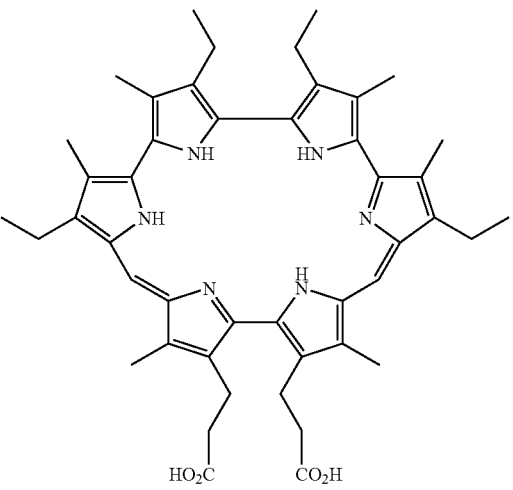

10. The compound of claim 1, wherein the compound has the formula:

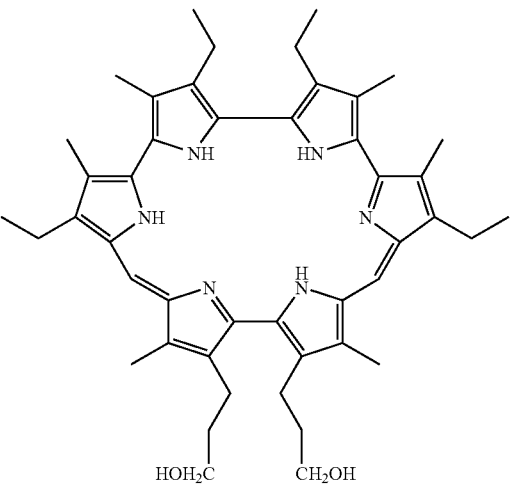

11. A composition comprising the compound of claim 1 and a solid support selected from the group consisting of silica gel, cellulose, glass, polyacrylamide, polystyrene-poly(ethylene glycol), and fiber optic.

12. The composition of claim 11, further comprising a $UO_2^{2+}$, $NpO_2^+$, $NpO_2^{2+}$, $PuO_2^+$, and $PuO_2^{2+}$.

13. A method of detecting the presence of an actinide cation in a sample, comprising: contacting the sample with the compound of claim 1, wherein a spectrometric change in the compound indicates the presence of the actinide cation.

* * * * *